US010010604B2

(12) United States Patent
Fachinger et al.

(10) Patent No.: US 10,010,604 B2
(45) **Date of Patent: *Jul. 3, 2018**

(54) TREATMENT OF PRDC IN PIGS

(71) Applicant: Boehringer Ingelheim Vetmedica, Inc., St. Joseph, MO (US)

(72) Inventors: Vicky Fachinger, Bad Soden (DE); Knut Elbers, Mittelbiberach (DE); Marion Kixmoeller, Munich (DE); Francois-Xavier Orveillon, Mainz (DE); Isabelle Freiin Von Richthofen, Charlottenlund (DK); Axel Lischewski, Ingelheim am Rheim (DE)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/346,919

(22) Filed: Nov. 9, 2016

(65) Prior Publication Data

US 2017/0049878 A1 Feb. 23, 2017

Related U.S. Application Data

(63) Continuation of application No. 14/740,238, filed on Jun. 15, 2015, now Pat. No. 9,522,182, which is a continuation of application No. 13/729,688, filed on Dec. 28, 2012, now abandoned, which is a continuation of application No. 13/024,119, filed on Feb. 9, 2011, now abandoned, which is a continuation of application No. 11/968,988, filed on Jan. 3, 2008, now Pat. No. 7,914,992.

(30) Foreign Application Priority Data

Jan. 3, 2007 (EP) .................................... 07100054

(51) Int. Cl.

*A61K 39/12* (2006.01)
*C12N 7/00* (2006.01)
*A61K 39/00* (2006.01)

(52) U.S. Cl.

CPC ................ *A61K 39/12* (2013.01); *C12N 7/00* (2013.01); *A61K 2039/5256* (2013.01); *A61K 2039/545* (2013.01); *A61K 2039/552* (2013.01); *A61K 2039/55555* (2013.01); *C12N 2710/14043* (2013.01); *C12N 2750/10022* (2013.01); *C12N 2750/10034* (2013.01)

(58) Field of Classification Search

None

See application file for complete search history.

(56) References Cited

U.S. PATENT DOCUMENTS

| | | | | |
|---|---|---|---|---|
| 5,476,778 | A | 12/1995 | Chladek et al. | |
| 7,109,025 | B1 | 9/2006 | Eloit et al. | |
| 7,223,407 | B2 | 5/2007 | Jestin et al. | |
| 7,829,101 | B2 | 11/2010 | Eichmeyer et al. | |
| 7,829,273 | B2 | 11/2010 | Roof et al. | |
| 7,829,274 | B2 | 11/2010 | Fachinger et al. | |
| 7,838,213 | B2 | 11/2010 | Roof et al. | |
| 7,838,214 | B2 | 11/2010 | Roof et al. | |
| 7,910,306 | B2 | 3/2011 | Eichmeyer et al. | |
| 7,914,992 | B2 | 3/2011 | Fachinger et al. | |
| 7,943,298 | B2 | 5/2011 | Fachinger et al. | |
| 7,968,285 | B2 | 6/2011 | Roof et al. | |
| 8,025,888 | B2 | 9/2011 | Eichmeyer et al. | |
| 8,119,143 | B2 | 2/2012 | Roof et al. | |
| 8,475,805 | B2 | 7/2013 | Fachinger et al. | |
| 8,496,940 | B2 | 7/2013 | Fachinger et al. | |
| 8,865,183 | B2 | 10/2014 | Fachinger et al. | |
| 9,011,868 | B2 | 4/2015 | Roof et al. | |
| 9,011,872 | B2 | 4/2015 | Eichmeyer et al. | |
| 9,132,187 | B2 | 9/2015 | Fachinger et al. | |
| 9,517,260 | B2 | 12/2016 | Fachinger et al. | |
| 9,522,182 | B2 * | 12/2016 | Fachinger .............. | A61K 39/12 |
| 9,555,092 | B2 | 1/2017 | Fachinger et al. | |
| 9,669,087 | B2 | 6/2017 | Roof et al. | |
| 2009/0010954 | A1 | 1/2009 | Fachinger et al. | |
| 2011/0033495 | A1 | 2/2011 | Roof et al. | |
| 2011/0091499 | A1 | 4/2011 | Fachinger et al. | |
| 2011/0129495 | A1 | 6/2011 | Fachinger et al. | |
| 2013/0115236 | A1 | 5/2013 | Fachinger et al. | |
| 2013/0273099 | A1 | 10/2013 | Fachinger et al. | |
| 2013/0302370 | A1 | 11/2013 | Fachinger et al. | |
| 2014/0377298 | A1 | 12/2014 | Fachinger et al. | |

(Continued)

FOREIGN PATENT DOCUMENTS

| | | | |
|---|---|---|---|
| WO | 2003068993 | A1 | 8/2003 |
| WO | 2005112995 | A1 | 12/2005 |

(Continued)

OTHER PUBLICATIONS

Boehringer Ingelheim Vetmedica, Inc., Ingelvacâ Circoflexä Material Safety Data Sheet, Online Oct. 2006, pp. 1-10, URL:http://bi-vetmedica.com/sites/default/files/ingelvac-circoflex-msds.pdf.
Chae, C. "A review of porcine circovirus 2-associated syndromes and diseases". The Veterinary Journal, vol. 169, No. 3, 2005, pp. 326-336.
Ellis et al., "Porcine circovirus-2 and concurrent infections in the field". Veterinary Microbiology, vol. 98, No. 2, Feb. 2004, pp. 159-163.
Fachinger et al., "The effect of vaccination against porcine circovirus type 2 in pigs suffering from porcine respiratory disease complex". 2008, Vaccine, vol. 26, pp. 1488-1499.
Fenaux et al., "A Chimeric Porcine Circovirus (PCV) with the Immunogenic Capsid Gene of the Pathogenic PCV Type 2 (PCV2) Clones into the Genomic Backbone of the Nonpathogenic PCV1 Induces Protective Imunity Against JCV2 Infection in Pigs", J. Virol, Jun. 2004, vol. 78, No. 12, pp. 6297-6303.

(Continued)

*Primary Examiner* — Shanon A. Foley
(74) *Attorney, Agent, or Firm* — Judy Jarecki-Black

(57) ABSTRACT

The present invention relates to the use of an immunogenic composition comprising a porcine circovirus type 2 (PCV2) antigen for the prevention and treatment, including a reduction in the severity of, duration of, and manifestations of, porcine respiratory disease complex (PRDC) in animals, preferably in pigs.

31 Claims, 1 Drawing Sheet

(56) References Cited

U.S. PATENT DOCUMENTS

2015/0273046 A1 10/2015 Fachinger et al.
2015/0343052 A1 12/2015 Fachinger et al.
2017/0049875 A1 2/2017 Roof et al.
2017/0049876 A1* 2/2017 Fachinger .............. A61K 39/12
2017/0087241 A1 3/2017 Fachinger et al.

FOREIGN PATENT DOCUMENTS

WO 2006072065 A2 7/2006
WO 2008081015 A1 7/2008
WO 2012033911 A2 3/2012
WO 2016160761 A2 10/2016

OTHER PUBLICATIONS

Gagrcin et al., "Complex of Swine Respiratory Diseases-Strategy of control in light of latest knowledge". Veterinarski Glasnik, vol. 58, No. 7-8, 2004, pp. 409-418. [English Abstract at p. 417.].
Harms et al., "Three cases of porcine respiratory disease complex associated with porcine circovirus type 2 infection". Journal of Swine Health and Production, vol. 10, No. 1, 2002, pp. 27-30.
International Search Report and Written Opinion for PCT/EP2008/050012 dated Mar. 31, 2008.
Kim et al., "Association of Porcine Circovirus 2 with Porcine Respiratory Disese Complex", The Vet. Jour., 2003, 166, pp. 251-256.
Opriessnig et al., "Experimental Reproduction of Postweaning Multisystemic Wasting Syndrome in Pigs by Dual Infection with Mycoplasma hyopneumoniae and Porcine Circovirus Type 2". Veterinary Pathology, vol. 41, No. 6, Nov. 2004, pp. 624-640.
Hu et al., "Baculovirus as a highly efficient expression vector in insect and mammalian cells." Acta Pharmacologica Sinica, vol. 26, No. 4, Apr. 2005, pp. 405-416.
Hulst et al., "Glycoprotein E1 of Hog Cholera Virus Expressed in Insect Cells Protects Swine from Hog Cholera." Journal of Virology, vol. 67, No. 9, Sep. 1993, pp. 5435-5442.
Insel et al., "Potential Alterations in Immunogenicity by Combining or Simultaneously Administering Vaccine Components." Annals of the New York Academy of Sciences, vol. 754, 1995, pp. 35-47.
Intervet Schering-Plough Animal Health, "Porcilis PRRS Data Sheet." 2011, pp. 1-3. [Accessed at http://www.intervet.co.uk/Products_Public/Porcilis_PRRS/Product_Datasheet.aspx on Apr. 12, 2011.].
Jensen, Poul Moesgaard, "The Danish SPF-System Developments and challenges in the future.", 2013, 18 pages. [Accessed at: http://giqs.org/fileadmin/web_giqs/content/PDFs/PDFs_Quarisma/projektplatfform/PDF_neu2013/SPF-Sundhedsstyringen_2013_QUARISMA_Holland.pdf].
Jensen, Poul Moesgaard, "The Danish SPF-Sytem Developments and challenges in the future." Quarisma-Workshop, May 16, 2013, pp. 1-18. [Accessed at: http://giqs.org/fileadmin/web_giqs/content/PDFs/PDFs_Quarisma/projektplattform/PDF_neu2013/SPF-Sundhedsstyringen_2013_QUARISMA_Holland.pdf].
King et al., "Insect cell culture media and maintenance of insect cell lines." The Baculovirus Expression System: A laboratory guide, First Edition, Springer-Science + Business Media, B.V., 1992, pp. 75-79.
Knudsen et al., "Child Mortality Following Standard, Medium or High Titre Measles Immunization in West Africa." International Journal of Epidemiology, vol. 25, No. 3, 1996, pp. 665-673.
Krakowka et al., "Activation of the Immune System is the Pivotal Event in the Production of Wasting Disease in Pigs Infected with Porcine Circovirus-2 (PCV-2)" Veterinary Pathology, vol. 38, 2001, pp. 31-42.
Krakowka et al., "Viral Wasting Sydrome of Swine: Experimental Reproduction of Postweaning Multisystemic Wasting Syndrome in Gnotobiotic Swine by Coinfection with Porcine Circovirus 2 and Porcine Parvovirus." Veterinary Pathology, vol. 37, 2000, pp. 254-263.
Larochelle et al., "Comparative serologic and virologic study of commerical swine herds with and without postweaning multisystemic wasting syndrom." The Canadian Journal of Veterinary Research, vol. 67, 2003, pp. 114-120.
Larochelle et al., "PCR Detection and Evidence of Shedding of Porcine Circovirus Type 2 in Boar Semen." Journal of Clinical Microbiology, vol. 38, No. 12, Dec. 2000, pp. 4629-4632.
Li et al., "Essential Elements of the Capsid Protein for Self-Assembly into Empty Virus-Like Particles of Hepatitis E Virus". Journal of Virology, vol. 79, No. 20, Oct. 2005, pp. 12999-13006.
Liesner et al., "Efficacy of Ingelvac CircoFLEX® in face of maternal antibodies in a field trial in France." 2008 Allen J. Leman Swine Conference—Recent Research Reports, p. 9.
Magar et al., "Experimental Transmission of Porcine Circovirus Type 2 (PCV2) in Weaned Pigs: a Sequential Study." Journal of Comparative Pathology, vol. 123, 2000, pp. 258-269.
McCall et al., "Improvements to the throughput of recombinant protein expression in the baculovirus/insect cell system." Protein Expression and Purification, vol. 42, 2005, pp. 29-36.
McNair et al., "Interlaboratory testing of porcine sera for antibodies to porcine circovirus type 2." Journal of Veterinary Diagnositc Investigation, vol. 16, 2004, pp. 164-166.
Meerts et al., "Correlation between the prsence of neutralizing antibodies against porcine circovirus 2 (PCV2) and protection against replication of the virus and development of PCV2-associated disease." BMV Veterinary Research, vol. 2, No. 6, 2006, pp. 1-11.
Meerts et al., "Correlation Between Type of Adaptive Immune Response Against Porcine Circovirus Type 2 and Level of Virus Replication." Viral Immunology, vol. 18, No. 2, 2005, pp. 333-341.
Merial Animal Health Ltd., "Progressis." 2011, pp. 1-2. [Accessed at http://www.noahcompendium.co.uk/Merial_Animal_Health_ltd/documents/53834.html on Apr. 12, 2011].
Midwest Research Swine, "High Health Heard Status." pp. 1-2. [Accessed at: http://midwestresearchswine.com/herd-health/high-health-herd-status/ on Jun. 27, 2016].
Moraes et al., "Drosophila melanogaster S2 cells for expression of heterologous genes: From gene cloning to bioprocess development." Biotechnology Advances, vol. 30, 2012, pp. 613-638.
Ng et al., "Extracellular self-assembly of virus-like particles from secreted recombinant polyoma virus major coat protein." Protein Engineering, Design & Selection, vol. 20, No. 12, 2007, pp. 591-598.
Niewiesk, Stefan, "Maternal antibodies: clinical significance, mechansim of interference with immune responses, and possible vaccination strategies." Frontiers in Immunology, vol. 5, Article 446, Sep. 2014, pp. 1-15.
O'Neill, Kevin Charles, "Efficacy and impact of current commercial porcine circovirus type 2 (PCV2) vaccines in dams and growing pigs." Graduate Theses and Dissertations, Graduate College, Iowa State University, Paper 12837, 2012, pp. 1-130.
Olejnik et al. "Effect of hyperosmolarity on recombinant protein productivity in baculovirus expression system." Journal of Biotechnology, vol. 102, 2003, pp. 291-300.
Onuki et al., "Detection of Porcine Circovirus from Lesions of a Pig with Wasting Disease in Japan." The Journal of Veterinary Medical Science, vol. 61, No. 10, Oct. 1999, pp. 1119-1123.
Pejawar-Gaddy et al., "Generation of a Tumor Vaccine Candidate Based on Conjugation of a MUC1 Peptide to Polyionic Papillomavirus Virus-Like Particles (VLPs)." Cancer Immunogy, Immunotherapy, vol. 59, No. 11, Nov. 2010, pp. 1648-1696.
Polo et al., "Half-life of porcine antibodies absorbed from a colostrum supplement containing porcine immunoglobulins." Journal of Animal Science, vol. 90, 2012, pp. 308-310.
Remington et al., "Active Immunizing Agents." Remington: The Science and Practice of Pharmacy, Twentieth Edition, 2000, p. 1569.
Reynaud et al., "Comparison of Clinical, Lesional and Virological Signs in Pigs With and Without Experimental PMWS" Proceedings of the 17th International Pig Veterinary Society Congress, Ames, Iowa, USA, Jun. 2002, vol. 1, p. 172.

(56) References Cited

OTHER PUBLICATIONS

Rossow et al., "Experimental porcine reproductive and respiratory syndrome virus infection in one-, four-, and 10-week-old pigs." Journal of Veterinary Diagnositc Investigations, vol. 6, 1994, pp. 3-12.
Rota et al., "Expression of influenza A and B virus nucleoprotein antigens in baculovirus." Journal of General Virology, vol. 71, 1990, pp. 1545-1554.
Safron et al., "The SPF Pig in Research." ILAR Journal, vol. 38, No. 1, 1997, pp. 28-31.
Sico et al., "Enhanced Kinetic Extraction of Parvovirus B19 Structural Proteins." Biotechnology and Bioengineering, vol. 80, No. 3, Nov. 5, 2002, pp. 250-256.
Siegrist et al., "Influence of maternal antibodies on vaccine responses: inhibition of antibody but not T cell responses allows successful early prime-boost strategies in mice." European Journal of Immunology, vol. 28, 1998, pp. 4138-4148.
Siegrist, Claire-Anne, "Mechanisms by which maternal antibodies influence infant vaccine responses: review of hypotheses and definition of main determinants." Vaccine, vol. 21, 2003, pp. 3406-3412.
Sigma-Aldrich®, "Product Information for TNM-FH Insert Media", 2014, 1 page.
Spear, Maynard L., "Specific Pathogen Free Swine." iowa State University Veterinarian, vol. 22, Iss. 3, Article 2, 1960, pp. 134, 136-137.
Stokka et al., "Modified-Live Vs. Killed Vaccines—Which is Better?" BeefMagazine.com, Oct. 2000, pp. 1-6. [Accessed at: http://beefmagazine.com/mag/beef_modifiedlive_vs_killed on Nov. 4, 2014].
Urniza et al., "Duration of Immunity Study in Pigs Vaccinated with an Inactivated/Adjuvanted Vaccine 'Chimeric Jorcine Circovirus Type 1/Type 2' in Front of a Challenge with PCV2 European Strain." Proccedings of the 19th IPVS Congress, Copenhagen, Denmark, vol. 2, Abstract No. P.07-09, 2006, p. 108.
Vidor, E. "The Nature and Consequences of Intra- and Inter-Vaccine Interference." Journal of Comparative Pathology, vol. 137, 2007, pp. S62-S66.
Viscidi et al., "Age-Specific Seroprevalence of Merkel Cell Polyomavirus, BK Virus, and JC Virus." Clinical and Vaccine Immunology, vol. 18, No. 10, Oct. 2011, pp. 1737-1743.
Warren et al., "Effect of Osmolality of the Cellular Microenvironment." Encyclopedia of Industrial Biotechnology: Bioprocess, Bioseparation, and Cell Technology: Animal Cells, Hybridomas, Human Antibody Production, John Wiley & Sons, Inc., 2010, pp. 1-16.
Wikipedia "Specific-pathogen-free". Wikipedia, The Free Encyclopedia, May 28, 2016, at 04:21, pp. 1-3 [Accessed at https://en.wikipedia.org/w/index.php?title=Specific-pathogen-free &oldid=722441484 on Jun. 27, 2016.
Yamaji et al., "Efficient production of Japanese encephalitis virus-like particles by recombinant lepidopteran insect cells." Applied Microbiology and Biotechnology, vol. 97, 2013, pp. 1071-1079.
Yamaji et al., "Optimal Production of Recombinant Protein by the Baculovirus-Insect Cell System in Shake-Flask Culture with Medium Replacement." Journal of Bioscience and Bioengineering, vol. 87, No. 5, 1999, pp. 636-641.
"5.2.9 Evaluation of Saftey of Each Batch of Veterinary Vaccines and Immunosera." European Pharmacopoeia, 5th Edition, Strasbourg: Council of Europe, 2005, pp. 2829-2830.
"Directive 2001/82/EC of the European Parliament and of the Council of Nov. 6, 2001 on the Community code relating to veterinary medicinal products." Official Journal of the European Communities, L 311, Nov. 2001, pp. 1-66.
"Killed vs. Modified Live Vaccines." DVMvac.org, 2006, pp. 1-3. [Accessed at http://dvmvac.org/killvmodified.asp on Oct. 10, 2017. ].
"Reflection paper on the demonstration of a possible impact of maternally derived antibodies on vaccine efficacy in young animals." Europan Medicines Agency: Science Medicines Health, Mar. 15, 2010, pp. 1-5.
9 C.F.R. Ch. 1 (1-1-06 Edition) §112.7(f), Animal and Plant Health Inspection Service, USDA, 1 page.
Allan et al., "Neonatal Vaccination for Mycoplasma Hyopneumoniae and Post-Weaning Multisystemic Wasting Syndrome: A Field Trial." The Pig Journal, vol. 48, 2001, pp. 34-41.
Bandrick et al., "Colostral antibody-mediated and cell-mediated immunity contributes to innate and antigen-specific immunity in piglets." Developmental and Comparative Immunology, vol. 43, 2014, pp. 114-120.
Berinstein et al., "Mucosal and systemic immunization elicited by Newcastle disease virus (NDV) transgenic plants as antigens." Vaccine, vol. 23, 2005, pp. 5583-5589.
Boehringer Ingelheim Vetmedica GmbH, "Our conviction regarding PRRS—only facts count!" Oct. 2003, pp. 1-3.
Boehringer Ingelheim Vetmedica, Inc., "Ingelvaca Circoflexa Safety Data Sheer" Apr. 27, 2015, pp. 1-6.
Boehringer Ingelheim Vetmedica, Inc., "ReproCyc® PRRS-PLE", 2011, p. 1. [Accessed at: http://bi-vetmedica.com/product/reprocyc-prrs-ple on Apr. 12, 2011].
Boehringer Ingelheim, "Preventing disease: One billion pigs vaccinated with Ingelvac CircoFLEX®" Feb. 14, 2013, pp. 1-3. [Available at: https://www.boehringer-ingelheim.com/press-release/preventing-disease-one-billion-pigs-vaccinated-ingelvac-circoflex].
Bretey et al., "Performance benefits resulting from vaccination with Ingelvac CircoFLEX and/or Ingelvac PRRS MLV." Leman Swine Conference 2009, 1 page.
Brockmeier et al., "Porcine Respiratory Disease Complex." Polymicrobial Diseases, Washington (DC), ASM Press; 2002, Chapter 13, pp. 1-25. [Accessed at https://www.ncbi.nlm.nih.gov/books/NBK2481/].
Bunn, Thomas O., "Vaccine Adjuvants and Carriers." Vaccines for Veterinary Applications, Oxford, Boston, Butterworth-Heinemann, 1993, pp. 295-302.
Cameo "Carbopol®". Wikipedia, The Free Encyclopedia, Jul. 24, 2013, at 06:59, pp. 1-2 [Accessed at https://http://cameo.mfa.org/index.php?title=Carbopol®&oldid=22637on Sep. 23, 2015].
Cariolet et al., "Rappel Des Différentes Méthodes D'Obtention de Porcelets Assainis: Conditions de Maintien Du Statut Sanitaire et Valorisation de ces Animaux." Journées Rech. Porcine en France, vol. 26, 1994, pp. 1-12. (Abstract in English on p. 1).
Charreyre et al., "Vaccination Concepts in Controlling PCV2-Associated Diseases." Merial, 18th IPVS, Hamburg (Germany), Jun. 2004, pp. 95-107.
Clark, Ted, "Pathology of the Postweaning Multisystemic Wastings Syndrome in Pigs." Proceedings of the Western Canadian Association of Swine Practitioners, 1996 Annual Meeting, Oct. 1996, pp. 22-25.
Csank et al., "Dynamics of antibody response and viraemia following natural infection of porcine circovirus 2 (PCV-2) in a conentional pig herd." Acta Pathologica, Microbiologica and Immunologica Scandinavica, vol. 121, 2012, pp. 1207-1213.
Cutts et al., "Immunogenicity of high-titre AIK-C or Edmonston-Zagreb vaccines in 3.5-month-old infants, and of medium- or high-titre Edmonston-Zagreb vaccine in 6-month-old infants, in Kinshasa, Zaire." Vaccine, vol. 12, No. 14, 1994, pp. 1311-1316.
Dehaven, W. Ron, "Veterinary Services Memorandum No. 800. 202." CVB General Licensing Considerations: Efficacy Stupies, Jun. 14, 2002, pp. 1-8.
Desrosiers et al., "Preliminary results with Ingelvac® CircoFLEX™ to protect multiple ages of Quebec Pigs against PCVAD." American Association of Swine Veterinarians, 2007, pp. 143-145.
Diamantstein et al., "Stimulation of humoral antibody formation by polyanions: I. The effect of polyacrylic acid on the primary immune response in mice immunized with sheep red blood cells." European Journal of Immunology, vol. 1, 1971, pp. 335-340.
Draganoiu et al., "Carbomer." Feb. 2009, pp. 110-114. [Retrieved at: http://drugs-nutrition.com/download/Handbook_of_excipients_6/Carbober.pdf on Sep. 23, 2015.].

(56) References Cited

OTHER PUBLICATIONS

Eddicks et al., "Low prevalence of porcine circovirus type 2 infections in farrowing sows and corresponding pre-suckling piglets in southern German pig farms." Veterinary Microbiology, vol. 187, 2016, pp. 70-74.
Eichmeyer et al., "Evaluation of Ingelvac® 3FLEX: Demonstration of efficacy for the mixture of Ingelvac® PRRS MLV when rehydrated with Ingelvac CircoFLEX® and Ingelvac MycoFLEX®". 2010 American Association of Swine Veterinarians Annual Conference, Mar. 6-9, 2010, pp. 1-5.
Eichmeyer, Marc, "Annex 1 of PCV-2 Study" Jan. 2012, pp. 1-2.
Eichmeyer, Marc, "Efficacy of a PCV-2 Antigen in a Combination Vaccne." Boehringer Ingelheim Vetmedica, Inc., Study No. 6131-0981-05P-022, PCV2 Combination Efficacy Study, Aug. 19, 2010, pp. 1-3.
Eichmeyer, Marc, "Efficacy of PPRS Antigen in a Combination Vaccne." Boehringer Ingelheim Vetmedica, Inc., Study No. 6131-0852-06P-072, Ingelvac® PRRS MLV Combination Vaccine Efficacy Study, Aug. 19, 2010, pp. 1-4.
Eichmeyer, Marc, "PCV-2 Study." Boehringer Ingelheim Vetmedica, Inc., Jan. 2012, pp. 1-4.
Eichmeyer, Marc, "Summary of Study No. 6127-0981-08P-044 (Efficacy Study)" Boehringer Ingelheim Vetmedica, Inc., Mar. 11, 2010, pp. 1-2.
Eichmeyer, Marc, "Summary of Study No. 6131-0981-04P-047 (Overdose Study)" Boehringer Ingelheim Vetmedmica, Inc., Mar. 11, 2010, pp. 1-2.
Eisele, Simon, "Determination of the efficacy of an inactivated one-shot vaccine in piglets during the first or third week of life with Porcilis® PCV." Inaugural Dissertation for the Obstetrics of Veterinary Medicine at the Faculty of Veterinary Medicine, Ludwig-Maximilians-Universitat Munchen, Jul. 17, 2009. (Summary in English beginning at p. 69), pp. 1-88.
European Medical Agency, "Annex I: Summary of Product Characteristics: Suvaxyn PCV Suspension for injection for pigs". EPAR Product Information, Last Updated Jun. 4, 2017, pp. 1-22. [Accessed at: http://www.ema.europa.eu/docs/en_GB/document_library/EPAR_-_Product_Information/veterinary/000149/WC500069200.pdf].
European Medicines Agency, "I. Background information on the Procedure." 2008, 2 pages. [Accessed at: http://www.ema.europa.eu/docs/en_GB/document_library/EPAR_-_Procedural_steps_taken_before_authorisation/veterinary/000126/WC500062386.pdf].
European Medicines Agency, "Ingelvac CircoFLEX: Procedureal steps taken and scientific information after the authorisation." 2015, pp. 1-3. [http://www.ema.europa.eu/docs/en_GB/document_library/EPAR_-_Procedural_steps_taken_and_scientitic_information_after_authorisation/veterinary/000126/WC500062387.pdf].
European Medicines Agency, "Scientific Discussion." 2008, pp. 1-18. [Accessed at: http://www.ema.europa.eu/docs/en_GB/document_library/EPAR_-_Scientific_Discussion/veterinary/000126/WC500062385.pdf].
Gerber et al., "Fetal infections and antibody profiles in pigs naturally infected with porcine circovirus type 2 (PCV2)." The Canadian Journal of Veterinary Research, vol. 76, 2012, pp. 38-44.
Goldenthal et al., "Overview-Combination Vaccines and Simultaneous Administration: Past, Present, and Future." Annals of the New York Academy of Sciences, vol. 754, 1995, ppxi-xiv.
Grau-Roma et al., "Recent advances in the epidemiology, diagnosis and control of diseases caused by porcine circovirus type 2." The Veterinary Journal, vol. 187, 2011, pp. 23-32.
Halbur et al., "Porcine Circovirus Associated Disease (PCVA) . . . a "Double Boger"." Carthage Veterinary Service ltd. 16th Annual Swine Conference, Jan. 1, 2006, 3 pages. [Accessed at http://www.prairieswine.com/porcine-circovirus-associated-disease-pcva%E2%80%A6-a-%E2%80%9Cdouble-bogey%E2%80%9D/ on Sep. 1, 2015].
Halbur et al., "Update on Porcine Circovirus Type 2 (PCV2)-Associated Diseases." Veterinary Diagnostic and Production Animal Medicine, Iowa State University, Ames, IA, 12th Annual Swine Disease Conference for Swine Practitioners, Nov. 2004, pp. 12-23.
Hallsworth et al., "Limits of life in MgCl2-containing environments: chaotropicity defines the window." Environmental Microbiology, vol. 9, No. 3, 2007, pp. 801-813.
Han et al., "Self-Assembly of the Recombinant Capsid Protein of a Bovine Norovirus (BoNV) into Virus-Like Particles and Evaluation of Cross-Reactivitiy of BoNV with Human Noroviruses." Journal of Clinical Microbiology, vol. 43, No. 2, Feb. 2005, pp. 778-785.
Harayama et al., "Maternal porcine circovirus type 2-memory T cells transfers to piglets through colostrums ingestion." Proceedings of the 5th Asian Pig Veterinary Society Congress Mar. 7-9, 2011, Pattaya, Thailand, pp. 82.
Harding et al., "Postweaning multisystemic wasting syndrome: Epidemiology and clincial presentation." Swine Health and Production, vol. 6, No. 6, 1998, pp. 249-254.
Harding, John C. "Post Weaning Multisystemic Wasting Syndrome (PMWS): Preliminary Epidemiology and Clinical Findings." Proceedings of the Western Canadian Association of Swine Practitioners, 1996 Annual Meeting, Oct. 1996, p. 21.
HiMedia Laboratories Pvt. Ltd., "TNM-FH Insect Medium With Lactalbumin hydrolysate, Yeast extract, L-Glutamine and Sodium bicarbonate 1X Liquid Insect Cell Culture Medium." Revision: Jan. 2013, pp. 1-2.
Hodgins et al., "Influence of age and maternal antibodies on antibody responses of neonatal piglets vaccinated against Mycoplasma hyopneumoniae." Journal of Swine Health and Production, vol. 12, No. 1, Jan.-Feb. 2004, pp. 10-16.
Charles River Laboraties International, Inc., "Indirect Fluorescent Antibody (IFA) Assay." Technical Sheet, V.2, 2011, pp. 1-2.
Robinson et al., "Immunofluorescence." IHC Staining Methods, Fifth Edition, Chapter 10, 2009, pp. 61-65.
Thomas et al., "Effect of PCV2 passive antibody levels on immunization with chimeric PCV1-2 vaccine and challenge with wild-type PCV2." American Association of Swine Veterinarians, 2005, pp. 23-25.
Vicente et al., "Epidemiological Study on Porcine Circovirus type 2 (PCV2) Infection in the European Wild Boar (SUS SCROFA) in Spain." Proceedings of the 18th IPVS Congress, vol. 1, Hamburg, Germany, 2004, p. 9.
Opriessnig et al., "Influence of anti-PCV2 passively-acquired antibodies on efficacy of Suvaxyn® PCV2 vaccination in pigs experimentally-infected with PCV2." American Association of Swine Veterinarians, 2007, pp. 299-300.
Boehringer Ingelheim Vetmedica, Inc. "Ingelvac® CircoFLEX™ Symposium." Sep. 15, 2007, St. Paul, Minnesota, pp. 1-8. [Accessed at http://animal-health-online.de/circovirus_01/docs/leman_circo.pdf].
Shi et al., "Protein N-Glycosylation in the Baculovirus-Insect Cell System." Current Drug Targets, vol. 8, No. 0, Oct. 2007, pp. 1116-1125.
Sequence Alignment of SEQ ID No. 1 with UniProt database access No. A7YF28_PCV2 by Li et al 2007.
Sequence Alignment of SEQ ID No. 1 with UniProt database access No. F8V1X0_PCV2 by Turcitu et al 2011.

* cited by examiner

TREATMENT OF PRDC IN PIGS

SEQUENCE LISTING

This application contains a sequence listing in paper format and in computer readable format, the teachings and content of which are hereby incorporated by reference. The sequence listing is identical with that incorporated in WO06/072065.

BACKGROUND OF THE INVENTION

Field of the Invention

The present invention relates to the use of an immunogenic composition comprising a porcine circovirus type 2 (PCV2) antigen for the prevention and treatment of porcine respiratory disease complex (PRDC) in animals, preferably in pigs.

Description of the Prior Art

Porcine circovirus type 2 (PCV2) is a small (17-22 nm in diameter), icosahedral, non-enveloped DNA virus, which contains a single-stranded circular genome. PCV2 shares approximately 80% sequence identity with porcine circovirus type 1 (PCV1). However, in contrast with PCV1, which is generally non-virulent, infection of swine with PCV2 has recently associated with a number of disease syndromes which have been collectively named Porcine Circovirus Diseases (PCVD) (also known as Porcine Circovirus associated Diseases (PCVAD)) (Allan et al, 2006, IPVS Congress). Postweaning Multisystemic Wasting Syndrome (PMWS) is generally regarded to be the major clinical manifestation of PCVD (Harding et al., 1997, Swine Health Prod; 5: 201-203; Kennedy et al., 2000, J Comp Pathol; 122: 9-24). PMWS affects pigs between 5-18 weeks of age. PMWS is clinically characterized by wasting, paleness of the skin, unthriftiness, respiratory distress, diarrhea, icterus, and jaundice. In some affected swine, a combination of all symptoms will be apparent while other affected swine will only have one or two of these symptoms (Muirhead, 2002, Vet. Rec.; 150: 456). During necropsy, microscopic and macroscopic lesions also appear on multiple tissues and organs, with lymphoid organs being the most common site for lesions (Allan and Ellis, 2000; J Vet. Diagn. Invest., 12: 3-14). A strong correlation has been observed between the amount of PCV2 nucleic acid or antigen and the severity of microscopic lymphoid lesions. Mortality rates for swine infected with PCV2 can approach 80%.

The extent of the involvement of PCV2 in swine diseases other than PMWS is currently poorly understood (Chae, Veterinary J., 2005; 169: 326-336). There are several potentially related conditions reported in the literature including porcine respiratory disease complex (PRDC), porcine dermatopathy and nephropathy syndrome (PDNS), reproductive failure, granulomatous enteritis and potentially, congenital tremors (CT-AII) and perinatal myocarditis (Chae, Veterinary J., 2005; 169: 326-336). Among these, PRDC is considered to have the greatest economical impact in Europe due to its general high prevalence, high morbidity rate (30-70% on affected farms) and mortality rate (4-6% on affected farms) (Kim et al., Veterinary J., 2003; 166: 251-256).

Pneumonia in pigs suffering from PRDC is due to a combination of both viral and bacterial agents such as PRRSV, Swine influenza virus (SIV), *Mycoplasma hyopneumoniae, Actinobacillus pleeuropneumoniae* and *Pasteurella multocida*. Although the aetiology involves multiple pathogens and varies from farm to farm, PRRSV and *Mycoplasma hyopneumoniae* are the two most common pathogens isolated from PCV2 positive pigs exhibiting PRDC (Kim et al., Veterinary J., 2003; 166: 251-256). Whether PCV2 plays any role in the cause of PRDC or in the manifestation, severity, or prolongation of clinical signs of PRDC is yet not known.

Compared with other viral pathogens PCV2 was consistently diagnosed in lung lesions of pigs suffering from PRDC. Prosepective studies have documented that pneumonia and often systemic illness, resulting from co-infection with PCV2 and PRRSV is more severe than that associated with infection by either agent alone. It can therefore be assumed that there is an apparent synergy between PCV2 and other pathogens that has been observed in respiratory disease cases in the field (Ellis et al., Veterinary Microbiol., 2004; 98: 159-163). However, it is yet not known whether PCV2, if present in pigs suffering from PRDC, has any influence on the clinical signs of PRDC in pigs. Due to the ubiquity of PCV2 with up to 100% seropositive animals at the end of fattening, it may similarly be possible that PCV2 has no influence at all on the disease expression of PRDC but is just an unrelated co-infecting agent.

Whereas PMWS mostly affects young pigs, typically between 5 and 12 weeks of age, PRDC is predominantely seen in growing to finishing pigs, typically around 16 to 22 weeks of age. The morbidity ranges from 30-70% with an average mortality of 4-6% (Kim et al., Veterinary J., 2003; 166: 251-256). Clinically signs of PRDC are prolonged and unusually severe cough and dyspnea that is refractory to antibiotic therapy, slow growth, decreased feed efficiency, lethargy, anorexia, and a marked increase in mortality in the middle to late phase of fattening.

A hallmark of microscopic lesions PRDC is bronchointerstitial pneumonia with peribronchial and peribronchiolar fibrosis. Alveolar septa are markedly thickened by infiltrates of macrophages (Chae, Veterinary J., 2005; 169: 326-336).

Approaches to treat PCV2 infections based on a DNA vaccine are described in U.S. Pat. No. 6,703,023. In WO 03/049703, production of a live chimeric vaccine is described, comprising a PCV-1 backbone in which an immunogenic gene of a pathogenic PCV2 strain replaces a gene of the PCV-1 backbone. WO99/18214 has provided several PCV2 strains and procedures for the preparation of a killed PVC2 vaccine. However, no efficacy data has been reported. An effective ORF-2 based subunit vaccine has been reported in WO06/072065, the teachings and content of which are incorporated by reference herein. Any of such vaccines are intended to be used for the vaccination/treatment of swine or pigs older than 3 weeks of age. None of these vaccines have been described for the prophylaxis or treatment of pigs suffering from PRDC, in particular in PCV2 positive pigs, suffering from PRDC.

Moreover, such vaccines have not been described to confer protective immunity against PCV2 infection or reducing, lessening the severity of, or curing any clinical symptoms associated therewith in pigs already having anti-PCV2 antibodies, preferably having maternal anti-PCV2 antibodies.

DISCLOSURE OF THE INVENTION

Figure 1:
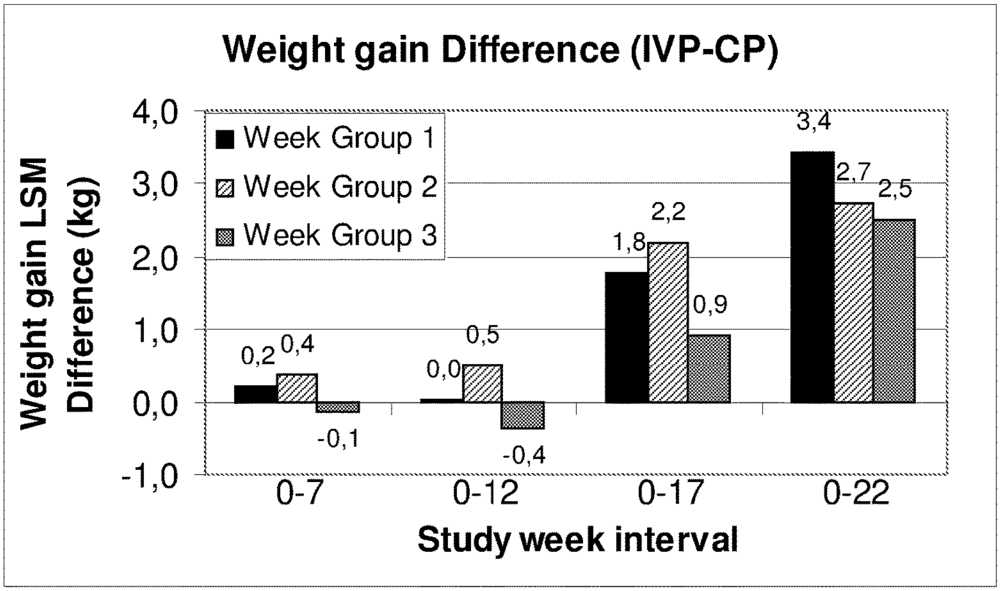
FIG. 1 is a graph illustrating body weight gain difference per week group.

PRDC is characterized by multiple clinical signs, including prolonged and unusually severe cough and dyspnea that is refractory to antibiotic therapy, slow growth, decreased feed efficiency, lethargy, anorexia, and a marked increase in mortality in the middle to late phase of fattening. Those clinical signs are associated with a large number of various pathogens. Involvement and, if any, the extent of involvement of PCV2 in PRDC was not known so far. It has been surprisingly found that among various pathogens, PCV2 also plays an important role in manifestation, severity and prolongation of clinical signs of PRDC. Thus among others, PCV2 is one of causative agents of PRDC in pigs.

In general, the impact of one causative agent on a multiple-cause disease (i.e., a multi-factorial disease) like PRDC is not predictable. A causative agent may have no effect but may also displace, repress, supersede, overlay or strengthen the effect of the others on the manifestation, severity and prolongation of clinical signs of a multi-factorial disease like PRDC. For example, reduction or elimination of one causative agent of a multi-factorial disease like PRDC may have no effect on the clinical appearance of that disease if at least one further causative agent is present, but it can also significantly reduce the clinical symptoms of that disease, even in the presence of any other causative agent. The higher the number of causative agents that are involved, the lower the expectation that a reduction or elimination of only one causative agent will have a positive influence on the duration of the manifestation, severity or prolongation of the disease. It has been surprisingly found now that manifestation, severity and prolongation of clinical signs of PRDC in pigs can be lessened or reduced by the prophylaxis or treatment of threatened or affected animals with PCV2 antigen.

In particular, the severity and prolongation of clinical signs of or associated with PRDC can strongly be lessened and reduced in pigs infected with PCV2 in combination with pathogens known to cause or be associated with PRDC in pigs, such as PRRSV, *Mycoplasma hyopneumoniae, Bordetella bronchiseptica*, Swine influenza virus, *Mycoplasma hyorhinis* and/or *Pasteurella multocida*. In other words, prophylaxis and treatment of pigs suffering from PRDC with PCV2 antigen has a positive impact on the overall health of the pigs. Furthermore, weight gain during fattening, and mortality in the middle to late phase of fattening of pigs are also positively impacted, which is a great benefit as these factors—overall health, weight gain, mortality—are known to be negatively affected by PRRSV, *Mycoplasma hyopneumoniae, Bordetella bronchiseptica*, Swine influenza virus, *Mycoplasma hyorhinis* and/or *Pasteurella multocida*.

Therefore, according to one aspect, the present invention provides a method for the prophylaxis and treatment of porcine respiratory disease complex (PRDC) and/or any clinical signs associated with PRDC in an animal, comprising the step of administering a therapeutically effective amount of PCV2 antigen or an immunogenic composition comprising a PCV2 antigen to an animal in need of such treatment.

The clinical signs associated with PRDC are selected from the group consisting of cough and dyspnea, slow growth, decreased feed efficiency, lethargy, anorexia, and/or a marked increase in mortality in the middle to late phase of fattening. Thus according to an other aspect, the present invention relates to a method for the prophylaxis and treatment of cough and dyspnea, slow growth, decreased feed efficiency, lethargy, anorexia, and/or a marked increase in mortality associated with PRDC in an animal, comprising the step of administering a therapeutically effective amount of PCV2 antigen or an immunogenic composition comprising a PCV2 antigen to an animal in need of such treatment. Preferably, the cough and dyspnea are refractory to antibiotic therapy.

The term "antigen" as used herein, refers to an amino acid sequence which elicits an immune response in a host. An antigen, as used herein, includes the full-length sequence of any PCV2 proteins, analogs thereof, or immunogenic fragments thereof. The term "immunogenic fragment" refers to a fragment of a protein which includes one or more epitopes and thus elicits the immune response in a host. Such fragments can be identified using any number of epitope mapping techniques well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, Jun. 28-Jul. 3, 1998.

An "immune response" means, but is not limited to, the development in a host of a cellular and/or antibody-mediated immune response to an antigen, an immunogenic composition or vaccine of interest. Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the symptoms associated with PCV2 infections, in delay of onset of viremia, in a reduced viral persistence, in a reduction of the overall viral load and/or a reduction of viral excretion.

The terms "immunogenic composition" or "vaccine" (both terms are used synonymously) as used herein refers to any pharmaceutical composition containing a PCV2 antigen, which composition can be used to prevent or treat a PCV2 infection-associated disease or condition in a subject. A preferred immunogenic composition can induce, stimulate or enhance the immune response against PCV2. The term thus encompasses both subunit immunogenic compositions, as described below, as well as compositions containing whole killed, or attenuated and/or inactivated PCV2.

Thus according to another aspect, the present invention relates to a method for the prophylaxis and treatment of porcine respiratory disease complex (PRDC) and/or any clinical signs associated with PRDC in an animal, comprising the step of administering an effective amount of PCV2 antigen or an immunogenic composition comprising an PCV2 antigen to that animal in need of such treatment, wherein the immunogenic composition is selected from the group consisting of a subunit immunogenic composition, a composition containing whole killed, or attenuated and/or inactivated PCV2, and combinations thereof.

The term "subunit immunogenic composition" as used herein refers to a composition containing at least one immunogenic polypeptide or antigen, but not all antigens, derived from or homologous to an antigen from PCV2. Such a composition is substantially free of intact PCV2. Thus, a "subunit immunogenic composition" is prepared from at least partially purified or fractionated (preferably substantially purified) immunogenic polypeptides from PCV2, or recombinant analogs thereof. A subunit immunogenic composition can comprise the subunit antigen or antigens of interest substantially free of other antigens or polypeptides from PCV2, or in fractionated from. A preferred immunogenic subunit composition comprises the PCV2 ORF-2 protein as described below. Most preferred are immunogenic subunit compositions, comprising any of the PCV2 antigens provided in WO06/072065, which are all incorporated herein by reference in their entirety.

According to further aspect, the immunogenic composition as used herein most preferably comprises the polypeptide, or a fragment thereof, expressed by ORF-2 of PCV2. PCV2 ORF-2 DNA and protein used herein for the preparation of the compositions and within the processes provided herein is a highly conserved domain within PCV2 isolates and thereby, any PCV2 ORF-2 would be effective as the source of the PCV ORF-2 DNA and/or polypeptide as used herein. A preferred PCV2 ORF-2 protein is that of SEQ ID NO: 11 herein and of WO06/072065. A further preferred PCV ORF-2 polypeptide is provided as SEQ ID NO: 5 herein and of WO06/072065. However, it is understood by those of skill in the art that this sequence could vary by as much as 6-10% in sequence homology and still retain the antigenic characteristics that render it useful in immunogenic compositions. The antigenic characteristics of an immunological composition can be, for example, estimated by the challenge experiment as provided by Example 4 of WO06/072065. Moreover, the antigenic characteristic of a modified antigen is still retained, when the modified antigen confers at least 70%, preferably 80%, more preferably 90% of the protective immunity as compared to the PCV2 ORF-2 protein, encoded by the polynucleotide sequence of SEQ ID NO:3 or SEQ ID NO:4 herein and as provided in WO06/072065.

Thus according to a further aspect, the present invention provides a method for the prophylaxis and treatment of porcine respiratory disease complex (PRDC) and/or any clinical signs associated with PRDC in an animal, comprising the step of administering an effective amount of PCV2 antigen or an immunogenic composition comprising a PCV2 antigen to that animal in need of such treatment, wherein the PCV2 antigen is an antigen of PCV2 ORF-2 protein that has at least 70%, preferably, 80% even more preferably 90% of the protective immunity as compared to compared to the PCV2 ORF-2 protein, encoded by the polynucleotide sequence of SEQ ID NO:3 or SEQ ID NO:4 as provided herein and in WO06/072065. Preferably said PCV2 ORF-2 will have the sequence of SEQ ID NO: 11 or SEQ ID NO: 5 herein and of WO06/072065.

In some forms, immunogenic portions of PCV2 ORF-2 protein are used as the antigenic component in the immunogenic composition, comprising PCV2 antigen. The term "immunogenic portion" as used herein refers to truncated and/or substituted forms, or fragments of PCV2 ORF-2 protein and/or polynucleotide, respectively. Preferably, such truncated and/or substituted forms, or fragments will comprise at least 6 contiguous amino acids from the full-length ORF-2 polypeptide. More preferably, the truncated or substituted forms, or fragments will have at least 10, more preferably at least 15, and still more preferably at least 19 contiguous amino acids from the full-length PCV ORF-2 polypeptide. Two preferred sequences in this respect are provided as SEQ ID NO: 9 and SEQ ID NO:10 herein and of WO06/072065. It is further understood that such sequences may be a part of larger fragments or truncated forms.

As mentioned above, a further preferred PCV2 ORF-2 polypeptide is any one encoded by the nucleotide sequences of SEQ ID NO: 3 or SEQ ID NO: 4. However, it is understood by those of skill in the art that this sequence could vary by as much as 6-20% in sequence homology and still retain the antigenic characteristics that render it useful in immunogenic compositions. In some forms, a truncated or substituted form, or fragment of this PVC2 ORF-2 polypeptide is used as the antigenic component in the composition. Preferably, such truncated or substituted forms, or fragments will comprise at least 18 contiguous nucleotides from the full-length PCV2 ORF-2 nucleotide sequence, e.g. of SEQ ID NO: 3 or SEQ ID NO: 4. More preferably, the truncated or substituted forms, or fragments, will have at least 30, more preferably at least 45, and still more preferably at least 57 contiguous nucleotides of the full-length PCV2 ORF-2 nucleotide sequence, e.g. SEQ ID NO: 3 or SEQ ID NO: 4.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferably at least 100, even more preferably at least 250, and even more preferably at least 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Thus, according to a further aspect, the present invention provides a method for the prophylaxis and treatment of porcine respiratory disease complex (PRDC) and/or any clinical signs associated with PRDC in an animal, comprising the step of administering an effective amount of PCV2 antigen or an immunogenic composition comprising a PCV2 antigen to that animal in need of such treatment, wherein said PCV2 ORF-2 protein is any one of those, described above. Preferably, said PCV2 ORF-2 protein is i) a polypeptide comprising the sequence of SEQ ID NO: 5, SEQ ID NO: 6, SEQ ID NO: 9, SEQ ID NO: 10 or SEQ ID NO: 11 herein and of WO06/07065;
ii) any polypeptide that is at least 80% homologous to the polypeptide of i),
iii) any immunogenic portion of the polypeptides of i) and/or ii)
iv) the immunogenic portion of iii), comprising at least 10 contiguous amino acids included in the sequences of SEQ ID NO: 5, SEQ ID NO: 6, SEQ ID NO: 9, SEQ ID NO: 10 or SEQ ID NO: 11 herein and of WO06/072065,
v) a polypeptide that is encoded by a DNA comprising the sequence of SEQ ID NO: 3 or SEQ ID NO: 4 herein and of WO06/072065.
vi) any polypeptide that is encoded by a polynucleotide that is at least 80% homologous to the polynucleotide of v),
vii) any immunogenic portion of the polypeptides encoded by the polynucleotide of v) and/or vi)
viii) the immunogenic portion of vii), wherein polynucleotide coding for said immunogenic portion comprises at least 30 contiguous nucleotides included in the sequences of SEQ ID NO: 3, or SEQ ID NO: 4 herein and of WO06/072065.

Preferably any of those immunogenic portions have the immunogenic characteristics of PCV2 ORF-2 protein that is encoded by the sequence of SEQ ID NO: 3 or SEQ ID NO: 4 herein and of WO06/07065.

According to a further aspect, PCV2 ORF-2 protein is provided in the immunogenic composition at an antigen inclusion level effective for inducing the desired immune response, namely reducing the incidence of, lessening the severity of, or preventing or reducing PRDC and/or any clinical symptoms associated with PRDC. Preferably, the PCV2 ORF-2 protein inclusion level is at least 0.2 μg antigen/ml of the final immunogenic composition (μg/ml), more preferably from about 0.2 to about 400 μg/ml, still more preferably from about 0.3 to about 200 μg/ml, even more preferably from about 0.35 to about 100 μg/ml, still more preferably from about 0.4 to about 50 μg/ml, still more preferably from about 0.45 to about 30 μg/ml, still more preferably from about 0.6 to about 15 μg/ml, even more preferably from about 0.75 to about 8 μg/ml, even more preferably from about 1.0 to about 6 μg/ml, still more preferably from about 1.3 to about 3.0 μg/ml, even more preferably from about 1.4 to about 2.5 μg/ml, even more preferably from about 1.5 to about 2.0 μg/ml, and most preferably about 1.6 μg/ml.

According to a further aspect, the PCV ORF-2 antigen inclusion level is at least 0.2 μg/PCV2 ORF-2 protein as described above per dose of the final antigenic composition (μg/dose), more preferably from about 0.2 to about 400 μg/dose, still more preferably from about 0.3 to about 200 μg/dose, even more preferably from about 0.35 to about 100 μg/dose, still more preferably from about 0.4 to about 50 μg/dose, still more preferably from about 0.45 to about 30 μg/dose, still more preferably from about 0.6 to about 15 μg/dose, even more preferably from about 0.75 to about 8 μg/dose, even more preferably from about 1.0 to about 6 μg/dose, still more preferably from about 1.3 to about 3.0 μg/dose, even more preferably from about 1.4 to about 2.5 μg/dose, even more preferably from about 1.5 to about 2.0 μg/dose, and most preferably about 1.6 μg/dose.

The PCV2 ORF-2 polypeptide used in the immunogenic composition in accordance with the present invention can be derived in any fashion including isolation and purification of PCV2 ORF2, standard protein synthesis, and recombinant methodology. Preferred methods for obtaining PCV2 ORF-2 polypeptide are provided in WO06/072065, the teachings and content of which are hereby incorporated by reference in its entirety. Briefly, susceptible cells are infected with a recombinant viral vector containing PCV2 ORF-2 DNA coding sequences, PCV2 ORF-2 polypeptide is expressed by the recombinant virus, and the expressed PCV2 ORF-2 polypeptide is recovered from the supernatant by filtration and inactivated by any conventional method, preferably using binary ethylenimine, which is then neutralized to stop the inactivation process.

The immunogenic composition as used herein also refers to a composition that comprises i) any of the PCV2 ORF-2 proteins described above, preferably in concentrations described above, and ii) at least a portion of the viral vector expressing said PCV2 ORF-2 protein, preferably of a recombinant baculovirus. Moreover, the immunogenic composition can comprise i) any of the PCV2 ORF-2 proteins described above, preferably in concentrations described above, ii) at least a portion of the viral vector expressing said PCV2 ORF-2 protein, preferably of a recombinant baculovirus, and iii) a portion of the cell culture supernatant.

Thus, according to a further aspect, the present invention provides a method for the prophylaxis and treatment of porcine respiratory disease complex (PRDC) and/or any clinical signs associated with PRDC in an animal, comprising the step of administering an effective amount of PCV2 antigen or an immunogenic composition comprising an PCV2 antigen to that animal in need of such treatment, wherein the PCV2 antigen is recombinant PCV2 ORF-2, and is preferably a baculovirus expressed PCV2 ORF-2. Preferably those recombinant or baculovirus expressed PCV2 ORF-2s have the sequence as described above.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, preferably of a recombinant baculovirus, and iii) a portion of the cell culture; wherein about 90% of the components have a size smaller than 1 μm.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) and inactivating agent to inactivate the recombinant viral vector preferably BEI, wherein about 90% of the components i) to iii) have a size smaller than 1 μm. Preferably, BEI is present in concentrations effective to inactivate the baculovirus, preferably in an amount of 2 to about 8 mM BEI, preferably of about 5 mM BEI.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) a neutralization agent to stop the inactivation mediated by the inactivating agent, wherein about 90% of the components i) to iii) have a size smaller than 1 μm. Preferably, if the inactivating agent is BEI, said composition comprises sodium thiosulfate in equivalent amounts to BEI.

The polypeptide is incorporated into a composition that can be administered to an animal susceptible to PCV2 infection. In preferred forms, the composition may also include additional components known to those of skill in the art (see also Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In a preferred embodiment, the immunogenic composition comprises PCV2 ORF-2 protein as provided herewith, preferably in concentrations described above, which is mixed with an adjuvant, preferably Carbopol, and physiological saline.

Those of skill in the art will understand that the composition used herein may incorporate known injectable, physiologically acceptable sterile solutions. For preparing a ready-to-use solutions for parenteral injection or infusion, aqueous isotonic solutions, such as e.g. saline or corresponding plasma protein solutions, are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Adjuvants" as used herein, can include aluminium hydroxide and aluminium phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.). JohnWiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among them, there may be mentioned Carbopol 974P, 934P and 971P. Most preferred is the use of Carbopol, in particular the use of Carbopol 971P, preferably in amounts of about 500 µg to about 5 mg per dose, even more preferred in an amount of about 750 µg to about 2.5 mg per dose and most preferred in an amount of about 1 mg per dose.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314, or muramyl dipeptide among many others.

Preferably, the adjuvant is added in an amount of about 100 µg to about 10 mg per dose. Even more preferably, the adjuvant is added in an amount of about 100 µg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

Additionally, the composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like. Most preferably, the composition provided herewith, contains PCV2 ORF-2 protein recovered from the supernatant of in vitro cultured cells, wherein said cells were infected with a recombinant viral vector containing PCV2 ORF-2 DNA and expressing PCV2 ORF-2 protein, and wherein said cell culture was treated with about 2 to about 8 mM BEI, preferably with about 5 mM BEI to inactivate the viral vector, and an equivalent concentration of a neutralization agent, preferably sodium thiosulfate solution to a final concentration of about 2 to about 8 mM, preferably of about 5 mM.

The present invention also relates to the use of an immunogenic composition for the prophylaxis or treatment of PRDC or the reduction of any clinical signs associated with PRDC that comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) a neutralization agent to stop the inactivation mediated by the inactivating agent, preferably sodium thiosulfate, in equivalent amounts to BEI; and vi) a suitable adjuvant, preferably Carbopol 971 in amounts described above; wherein about 90% of the components i) to iii) have a size smaller than 1 µm. According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic composition as used herein also refers to a composition that comprises per one ml i) at least 1.6 µg of PCV2 ORF-2 protein described above, ii) at least a portion of baculovirus expressing said PCV2 ORF-2 protein iii) a portion of the cell culture, iv) about 2 to 8 mM BEI, v) sodium thiosulfate in equivalent amounts to BEI; and vi) about 1 mg Carbopol 971, and vii) phosphate salt in a physiologically acceptable concentration; wherein about 90% of the components i) to iii) have a size smaller than 1 µm and the pH of said immunogenic composition is adjusted to about 6.5 to 7.5.

The immunogenic compositions can further include one or more other immuno-modulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, the present invention contemplates compositions comprising from about 50 µg to about 2000 µg of adjuvant and preferably about 250 µg/ml dose of the vaccine composition. Thus, the immunogenic composition as used herein also refers to a composition that comprises from about 1 ug/ml to about 60 µg/ml of antibiotics, and more preferably less than about 30 µg/ml of antibiotics.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; vi) a suitable adjuvant, preferably Carbopol 971 in amounts described above; vii) a pharmaceutical acceptable concentration of a saline buffer, preferably of a phosphate salt, and viii) an anti-microbiological active agent; wherein about 90% of the components i) to iii) have a size smaller than 1 μm.

The immunogenic composition as used herein also refers to Ingelvac® CircoFLEX™, (Boehringer Ingelheim Vetmedica Inc, St Joseph, Mo., USA), CircoVac® (Merial SAS, Lyon, France), Porcilis PCV (Intervet Inc., Millsboro, Del., USA), or Suvaxyn PCV-2 One Dose® (Fort Dodge Animal Health, Kansas City, Kans., USA). Thus, the present invention also provides a method for the prophylaxis and treatment of porcine respiratory disease complex (PRDC) and/or any clinical signs associated with PRDC in an animal, comprising the step of administering a therapeutically effective amount of PCV2 antigen or an immunogenic composition comprising an PCV2 antigen to an animal in need of such treatment, wherein wherein said immunogenic composition comprising an PCV2 antigen is Ingelvac® CircoFLEX™, CircoVac®, Porcilis PCV and/or Suvaxyn PCV-2 One Dose®, preferably it is Ingelvac® CircoFLEX™.

As described above, PCV2 has been identified to be one relevant causative agent of PRDC. Most of the pigs suffering from PRDC are positive for PCV2 (e.g. Kim et al., Veterinary Journal (2003) 166: 251-256). The treatment of pigs with PCV2 antigen results in the reduction of the respiratory symptoms of PRDC (see Example 3). Thus according to a further aspect, the present invention provides a method for the prophylaxis and treatment of porcine respiratory disease complex (PRDC) and/or any clinical signs associated with PRDC in an animal, comprising the step of administering a therapeutically effective amount of PCV2 antigen or an immunogenic composition comprising a PCV2 antigen to an animal in need of such treatment, wherein the PRDC or the clinical signs associated with PRDC is/are associated with or caused by PCV2. Moreover, the present invention also provides a method for the prophylaxis and treatment of porcine respiratory disease complex (PRDC) and/or any clinical signs associated with PRDC in an animal, comprising the step of administering a therapeutically effective amount of PCV2 antigen or an immunogenic composition comprising an PCV2 antigen to an animal in need of such treatment, wherein the PRDC or the clinical signs associated with PRDC is/are associated with or caused by PCV2 and PRRSV, *Actinobacillus pleuropneumoniae, Mycoplasma hyopneumoniae, Bordetella bronchiseptica*, Swine influenza virus, *Mycoplasma hyorhinis, Streptococcus suis* and/or *Pasteurella multocida.*

As PCV2 is one of the causative agents of PRDC, herds which are positive for PCV2 bear a higher risk of developing PRDC or of developing a more serious duration of PRDC with serious clinical symptoms than PCV2 free herds. The term "herd that is positive for PCV2" as used herein means that at least 1% preferably 10%, more preferably 30%, even more preferably 50%, most preferably 70% of the animals of a herd are infected or become infected to any time with PCV2. This does not necessarily mean, that any animal of the herd develops clinical symptoms known to be caused by PCV2, such as PMWS or PRDC. Thus according to a further aspect, the present invention also provides a method for the prophylaxis and treatment of porcine respiratory disease complex (PRDC) and/or any clinical signs associated with PRDC in an animal, comprising the step of administering a therapeutically effective amount of PCV2 antigen or an immunogenic composition comprising a PCV2 antigen to an animal in need of such treatment, wherein the animal belongs to a herd that is positive for PCV2. Preferably, the PRDC and/or any clinical signs associated with PRDC are caused by PCV2.

As PRDC and the clinical symptoms of PRDC can also be lessened or reduced in the in animals that are co-infected with other causative pathogens of PRDC, the present invention also provides a method for the prophylaxis and treatment of porcine respiratory disease complex (PRDC) and/or any clinical signs associated with PRDC in an animal, comprising the step of administering a therapeutically effective amount of PCV2 antigen or an immunogenic composition comprising a PCV2 antigen to an animal in need of such treatment, wherein the animal belongs to a herd that is positive for PCV2 and one or more further pathogen(s) selected from the group consisting of PRRSV, *Mycoplasma hyopneumoniae, Actinobacillus pleuropneumoniae, Bordetella bronchiseptica*, Swine influenza virus, *Mycoplasma hyorhinis, Streptococcus suis* and/or *Pasteurella multocida*. Preferably, the PRDC and/or any clinical signs associated with PRDC are caused by PCV2 and at least one other PRDC causing pathogen. The term "a herd that is positive for PCV2 and one or more further pathogen(s) selected from the group consisting of PRRSV, *Mycoplasma hyopneumoniae, Actinobacillus pleuropneumoniae, Bordetella bronchiseptica*, Swine influenza virus, *Mycoplasma hyorhinis, Streptococcus suis* and/or *Pasteurella multocida*", as used herein means, that at least 10%, preferably 30%, more preferably 50%, even more preferably 70% of the animals of a herd are infected or become infected at any time with PCV2 and at least one of the further pathogens listed below. This does not necessarily mean, that any animal of the herd develops clinical symptoms known to be caused by PCV2 and at least one of the pathogens listed above, e.g. PRDC. Preferably, the PRDC and/or any clinical signs associated with PRDC are caused at least by PCV2.

PRDC does not only affect a defined number of animals, it normally affects all animals of herd (the whole herd). In other words, if at least one animal of a farm develops PRDC, the causative agents of PRDC are presistenly present within the live stock of that farm. Thus according to a further aspect, the present invention also provides a method for the prophylaxis and treatment of porcine respiratory disease complex (PRDC) and/or any clinical signs associated with PRDC in an animal, comprising the step of administering a therapeutically effective amount of PCV2 antigen or an immunogenic composition comprising a PCV2 antigen to an animal in need of such treatment, wherein the animal belongs to a herd that is positive for PCV2. Preferably, the PRDC and/or any clinical signs associated with PRDC are caused by PCV2. The term "a herd that is positive for PCV2" as used herein means that at least 1% preferably 10%, more preferably 30%, even more preferably 50%, and most preferably 70% of the animals of a herd are infected or become infected to at any time with PCV2. This does not necessarily mean, that any animal of the farm develops clinical signs known to be caused by PCV2, such as PMWS or PRDC. Preferably, the PRDC and/or any clinical signs associated with PRDC are caused by PCV2.

As PRDC and the clinical symptoms of PRDC can also be lessened or reduced in animals that are co-infected with other causative pathogens of PRDC, the present invention also provides a method for the prophylaxis and treatment of porcine respiratory disease complex (PRDC) and/or any clinical signs associated with PRDC in an animal, comprising the step of administering a therapeutically effective amount of PCV2 antigen or an immunogenic composition comprising a PCV2 antigen to an animal in need of such treatment, wherein the animal belonging to a farm that is positive for PCV2 and one or more further pathogen(s) are selected from the group consisting of PRRSV, *Mycoplasma hyopneumoniae, Actinobacillus pleuropneumoniae, Bordetella bronchiseptica*, Simian influenza virus, *Mycoplasma hyorhinis, Streptococcus suis* and/or *Pasteurella multocida*. Preferably, the PRDC and/or any clinical signs associated with PRDC are caused by PCV2 and at least one other PRDC causing pathogen. The term "a herd that is positive for PCV2 and one or more further pathogen(s) selected from the group consisting of PRRSV, *Mycoplasma hyopneumoniae, Actinobacillus pleuropneumoniae, Bordetella bronchiseptica*, Swine influenza virus, *Mycoplasma hyorhinis* and/or *Pasteurella multocida*", as used herein means, that at least 10%, preferably 30%, more preferably 50%, even more preferably 70% of the animals of a herd are infected or become infected to at any time with PCV2 and at least one of the further pathogens listed below. This does not necessarily mean, that any animal of the herd develops clinical symptoms known to be caused by PCV2 and at least one of the pathogens listed above, e.g. PRDC.

Maternally derived immunity has been shown to confer a certain degree of protection against PCV2 infection and clinical diseases associated with PCV2 infections. This protection has been shown to be titer dependent: higher titers are generally protective whereas lower titers are not (McKeown et al., 2005; Clin. Diagn. Lab. Immunol.; 12: 1347-1351). The mean antibody half-life in weanlings has been estimated to be 19.0 days and the window for PCV2-passive antibody decay within a population is relatively wide (Opriessnig et al. 2004, J. Swine Health Prod. 12:186-191). The presence of maternally derived antibodies not only may confer a certain degree of protection against viral infections, which however is not predictable, but may also be known to impair the efficacy of immunization. It has surprisingly been found, that the presence of anti-PCV2 antibodies, in particular of anti-PCV2 antibody titers of up to 1:20480, does not affect the efficacy of the PCV2 treatment. Thus according to a further aspect, the present invention provides a method for the prophylaxis and treatment of porcine respiratory disease complex (PRDC) and/or any clinical signs associated with PRDC in an animal, comprising the step of administering a therapeutically effective amount of PCV2 antigen or an immunogenic composition comprising a PCV2 antigen to an animal in need of such treatment having anti-PCV2 antibodies, preferably wherein said animal has a detectable anti-PCV2 antibody titer of up to 1:100, preferably of more than 1:100, even more preferably of more than 1:250, even more preferably of more than 1:500, even more preferably of 1:640; even more preferably of more than 1:750, most preferably of more than 1:1000. Preferably, those anti-PCV2 antibody titers are detectable and quantifiable in a specific anti-PCV2 immune assay, preferably in the assay as described in Example 2.

Methods for the detection and quantification of anti-PCV2 antibodies are well known in the art. For example detection and quantification of PCV2 antibodies can be performed by indirect immunofluorescence as described in Magar et al., 2000, Can. J. Vet Res.; 64: 184-186 or Magar et al., 2000, J. Comp. Pathol.; 123: 258-269. Further assays for quantification of anti-PCV2 antibodies are described in Opriessnig et al., 2006, 37$^{th}$ Annual Meeting of the American Association of Swine Veterinarians. Moreover, Example 2 also describes an indirect immunofluorescence assay, that can be used by a person skilled in the art. In cases of controversial results and in any question of doubt, anti-PCV2 titers as mentioned herein, refer to those which are/can be estimated by the assay as described in Example 2.

According to a further, more general aspect, the present invention provides a method for the prophylaxis of PRDC, preferably associated with or caused by PCV2, or for reduction of clinical symptoms caused by or associated with PRDC in young animals, comprising the step of administering an effective amount of a PCV2 antigen to that young animal in need of such treatment.

The term "young animal" as used herein refers to an animal of 1 to 22 days of age. Preferably, by the term young animal, an animal of 1 to 20 days of age is meant. More preferably, the term young animal refers to an animal of 1 to 15 days of age, even more preferably of 1 day of age to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably of 1 or 2 day(s) of age, most preferably to an animal of 1 day of age. Thus according to a further aspect, the present invention provides a method for the prophylaxis of PRDC, preferably associated with or caused by PCV2, or for reduction of clinical symptoms caused by or associated with PRDC in young animals, comprising the step of administering an effective amount of a PCV2 antigen to an animal of 1 to 22 days of age, preferably of 1 to 20 days of age, more preferably of 1 to 15 days of age, even more preferably of 1 to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably of 1 or 2 day(s) of age, most preferably at 1 day of age in need of such treatment. For example evidence is given that vaccination/treatment on 19 to 22 days of age shows or provides high efficacy of vaccination. Moreover, vaccination/treatment at days 12 to 18 of age has also be shown to be very effective in reducing clinical symptoms associated with or caused by PRDC, reduction of overall viral load, reduction of duration of viremia, delay in onset of viremia, and weight gain.

Due to the ubiquity of PCV2 in the field, most of the young piglets are seropositve in respect to PCV2. Thus according to a further aspect, the present invention provides a method for the prophylaxis of PRDC, preferably associated with or caused by PCV2, or for the reduction of clinical symptoms caused by or associated with PRDC in young animals having anti-PCV2 antibodies, preferably at the day of vaccination, comprising the step of administering an effective amount of a PCV2 antigen to an animal of 1 to 22 days of age, preferably of 1 to 20 days of age, more preferably of 1 to 15 days of age, even more preferably of 1 to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably at 1 or 2 day(s) of age, most preferably at 1 day of age in need of such treatment. Preferably, said young animals, at the day of vaccination/treatment, have a detectable anti-PCV2 antibody titer of up to 1:100, preferably of more than 1:100, even more preferably of more than 1:250, even more preferably of more than 1:500, even more preferably of more than 1:640, even more preferably of more than 1:750, and most preferably of more than 1:1000 at the day of vaccination/treatment.

As described above, vaccination/treatment of animals suffering from PRDC with PCV2 antigen resulted in a shortening of viremic phase as compared to non vaccinated control animals. The average shortening time was 15.4 days as compared to non vaccinated control animals of the same species. Therefore, according to a further aspect, the present invention also provides a method for the treatment or prophylaxis of PRDC, preferably associated with or caused by PCV2, or for reduction of clinical symptoms caused by or associated with PRDC in animals, comprising the step of administering an effective amount of a PCV2 antigen to that animal in need of such treatment, wherein the treatment or prophylaxis results in shortening of the viremia phase of 5 or more days, preferably 6 or more days, even more preferably of 7 or more days, even more preferably of 8 or more days, even more preferably of 9, even more preferably of 10, even more preferably of 12, even more preferably of 14, most preferably of more than 15 days as compared to animals of a non-treated control group of the same species.

In general, the vaccination of pigs suffering from PRDC resulted in a reduction in the loss of weight gain, reduction in clinical respiratory signs such as cough and dyspnea, a shorter duration of viremia, an earlier end to viremia, and a lower virus load. Therefore, according to a further aspect, the present invention provides a method for the treatment or prophylaxis of PRDC, preferably associated with or caused by PCV2, or for reduction of clinical symptoms associated with or caused by PRDC in animals, comprising the step of administering an effective amount of PCV2 antigen to an animal in need of such treatment, wherein said treatment or prophylaxis results in an improvement in comparison to animals of a non-treated control group of the same species in a vaccine efficacy parameter selected from the group consisting of a reduction in the loss of weight gain, reduction in clinical respiratory signs such as cough and dyspnea, a shorter duration of viremia, an earlier end to viremia, a lower virus load, or combinations thereof.

The term "an effective amount" as used herein means but is not limited to an amount of antigen, that elicits or is able to elicit an immune response in an animal, to which said effective dose of PCV2 antigen is administered.

The amount that is effective depends on the ingredients of the vaccine and the schedule of administration. Typically, when an inactivated virus or a modified live virus preparation is used in the combination vaccine, an amount of the vaccine containing about $10^{2.0}$ to about $10^{9.0}$ $TCID_{50}$ per dose, preferably about $10^{3.0}$ to about $10^{8.0}$ $TCID_{50}$ per dose, more preferably, about $10^{4.0}$ to about $10^{8.0}$ $TCID_{50}$ per dose. In particular, when modified live PCV2 is used in the vaccines, the recommended dose to be administered to the susceptible animal is preferably about $10^{3.0}$ $TCID_{50}$ (tissue culture infective dose 50% end point)/dose to about $10^{6.0}$ $TCID_{50}$/dose and more preferably about $10^{4.0}$ $TCID_{50}$/dose to about $10^{5.0}$ $TCID_{50}$/dose. In general, the quantity of antigen will be between 0.2 and 5000 micrograms, and between $10^{2.0}$ and $10^{9.0}$ $TCID_{50}$, preferably between $10^{3.0}$ and $10^{6.0}$ $TCID_{50}$, more preferably between $10^{4.0}$ and $10^{5.0}$ $TCID_{50}$, when purified antigen is used.

Sub-unit vaccines are normally administered with an antigen inclusion level of at least 0.2 μg antigen per dose, preferably with about 0.2 to about 400 μg/dose, still more preferably with about 0.3 to about 200 μg/dose, even more preferably with about 0.35 to about 100 μg/dose, still more preferably with about 0.4 to about 50 μg/dose, still more preferably with about 0.45 to about 30 μg/dose, still more preferably with about 0.6 to about 16 μg/dose, even more preferably with about 0.75 to about 8 μg/dose, even more preferably with about 1.0 to about 6 μg/dose, still more preferably with about 1.3 to about 3.0 μg/dose.

Unexpectedly, it was found that the prophylactic use of the immunogenic compositions described supra, is effective for the reduction of clinical symptoms caused by or associated with PRDC, preferably caused at least by PCV2 in animals. Moreover, the antigenic composition described herein reduces the overall circovirus load including a later onset, a shorter duration, an earlier end of viremia, and a reduced viral load and its immunosuppressive impact in animals suffering from PRDC, and thereby resulting in a higher level of general disease resistance and a reduced incidence of PRDC.

The composition according to the invention may be applied intradermally, intratracheally, or intravaginally. The composition preferably may be applied intramuscularly or intranasally, most preferably intramuscularly. In an animal body, it can prove advantageous to apply the pharmaceutical compositions as described above via an intravenous or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the compositions according to the invention may be administered once or several times, also intermittently, for instance on a daily basis for several days, weeks or months and in different dosages.

Preferably, at least one dose of the immunogenic composition as described above is intramuscularly administered to the subject in need thereof. According to a further aspect, the PCV2 antigen or the immunogenic composition comprising any such PCV2 antigen as described herein is bottled in and administered at one (1) mL per dose. Thus, according to a further aspect, the present invention also provides a 1 ml immunogenic composition, comprising PCV-2 antigen as described herein, for the treatment or prophylaxis of porcine respiratory disease complex (PRDC) and/or any clinical signs associated with PRDC, preferably caused by PCV2, in animals, comprising the step of administering an effective amount of a PCV2 antigen to that animal in need of such treatment.

According to a further aspect, at least one further administration of at least one dose of the immunogenic composition as described above is given to a subject in need thereof, wherein the second or any further administration is given at least 14 days beyond the initial or any former administrations. Preferably, the immunogenic composition is administered with an immune stimulant. Preferably, said immune stimulant is given at least twice. Preferably, at least 3 days, more preferably at least 5 days, even more preferably at least 7 days are in between the first and the second or any further administration of the immune stimulant.

Preferably, the immune stimulant is given at least 10 days, preferably 15 days, even more preferably 20, even more preferably at least 22 days beyond the initial administration of the immunogenic composition provided herein. A preferred immune stimulant is, for example, keyhole limpet hemocyanin (KLH), preferably emulsified with incomplete Freund's adjuvant (KLH/ICFA). However, it is herewith understood, that any other immune stimulant known to a person skilled in the art can also be used. The term "immune stimulant" as used herein, means any agent or composition that can trigger the immune response, preferably without initiating or increasing a specific immune response, for example the immune response against a specific pathogen. It is further instructed to administer the immune stimulant in a suitable dose.

The present invention also relates to the use of a PCV2 antigen or an immunogenic composition comprising PCV2 antigen for the preparation of a medicine for the prophylaxis and treatment of porcine respiratory disease complex (PRDC) and/or any clinical sign associated with PRDC in an animal. Preferably, the PRDC or the clinical signs associated with PRDC are caused at least PCV2, more preferably in combination with one or more further pathogens selected from the group consiting of of PRRSV, *Mycoplasma hyopneumoniae, Actinobacillus pleuropneumoniae, Bordetella bronchiseptica*, Simian influenza virus, *Mycoplasma hyorhinis, Streptococcus suis* and/or *Pasteurella multocida*. More preferably, the PCV2 antigen is a recombinant antigen, preferably PCV2 ORF-2, even more preferably Ingelvac® CircoFLEX™.

The "animal" as used herein means a swine, pig or piglet. Thus, according to a further aspect, the present invention provides a method for the prophylaxis and treatment of porcine respiratory disease complex (PRDC) and/or any clinical signs associated with PRDC in a pig, comprising the step of administering a therapeutically effective amount of PCV2 antigen or an immunogenic composition comprising an PCV2 antigen to an animal in need of such treatment. Preferably, the PRDC is caused at least by PCV2, preferably in combination with at least one further aetiologic agent known to cause PRDC, e.g. PRRSV, *Mycoplasma hyopneumoniae, Actinobacillus pleuropneumoniae, Bordetella bronchiseptica*, Swine influenza virus, *Mycoplasma hyorhinis, Streptococcus suis* and/or *Pasteurella multocida*. Preferably, the PCV2 antigen or immunogenic composition comprising PCV2 antigen is anyone of those described supra, most preferably the PCV2 antigen is Ingelvac® CircoFLEX™.

DETAILED DESCRIPTION OF THE PREFERRED EMBODIMENTS

The following examples set forth preferred materials and procedures in accordance with the present invention. Although any methods and materials similar or equivalent to those described herein can be used in the practice or testing of the present invention, the preferred methods, devices, and materials are now described. It is to be understood, however, that these examples are provided by way of illustration only, and nothing therein should be deemed a limitation upon the overall scope of the invention.

Example 1

Preparation of PCV2 ORF-2 Antigen

Initial SF+ cell cultures from liquid nitrogen storage were grown in Excell 420 media (JRH Biosciences, Inc., Lenexa, Kans.) in suspension in sterile spinner flasks with constant agitation. The cultures were grown in 100 mL to 250 mL spinner flasks with 25 to 150 mL of Excell 420 serum-free media. When the cells had multiplied to a cell density of $1.0\text{-}8.0\times10^6$ cells/mL, they were split to new vessels with a planting density of $0.5\text{-}1.5\times10^6$ cells/mL. Subsequent expansion cultures were grown in spinner flasks up to 36 liters in size or in stainless steel bioreactors of up to 300 liters for a period of 2-7 days at 25-29° C.

After seeding, the flasks were incubated at 27° C. for four hours. Subsequently, each flask was seeded with a recombinant baculovirus containing the PCV2 ORF-2 gene (SEQ ID NO: 4). The recombinant baculovirus containing the PCV2 ORF-2 gene was generated as described in WO06/072065. After being seeded with the baculovirus, the flasks were then incubated at 27±2° C. for 7 days and were also agitated at 100 rpm during that time. The flasks used ventilated caps to allow for air flow.

After incubation, the resulting supernatant were harvested, filtered in order to remove cell debris, and inactivated. The supernatant was inactivated by bringing its temperature to 37±2° C. and binary ethlylenimine (BEI) was added to the supernatant to a final concentration of 5 mM. The samples were then stirred continuously for 72 to 96 hrs. A 1.0 M sodium thiosulfate solution to give a final minimum concentration of 5 mM was added to neutralize any residual BEI. After inactivation, PCV2 ORF-2 buffered with phosphate buffer and Carbopol was added to about 0.5 to 2.5 mg/dose. The final dose comprises about 16 μg PCV2 ORF-2 antigen.

Example 2

Anti PCV-2 Immuno Assay

PK15 (e.g. ATCC CCL-33) or VIDO R1 cells described in WO 02/07721, are seeded onto a 96 well plate (about 20.000 to 60.000 cells per wells). Cells are infected with a PCV2 isolate, when monolayers are approximately 65 to 85% confluent. Infected cells are incubated for 48 hours. Medium is removed and wells are washed 2 times with PBS. The wash buffer is discarded and cells are treated with cold 50/50 methanol/acetone fixative (~100 μl/well) for about 15 mm at about −20° C. The fixative is discarded and the plates are air dried. Serial dilutions of porcine serum samples are prepared in PBS, added to the plates and incubated to allow antibodies to bind if present in the serum samples for about 1 hr at 36.5±1° C. In addition, serial dilutions of an anti-PCV2 positive and negative control sample (Positive Control and Negative Control Samples) are run in parallel. The plates are then washed three times with PBS. The PBS is discarded. Plates are then stained with a commercial Goat anti-Swine FITC conjugate diluted 1:100 in PBS and incubated for about 1 hr at 36.5±1° C., which allows detection of antibodies bound to infected cells. After incubation is complete, the microplates are removed from incubator, the conjugate is discarded and the plates are washed 2 times with PBS. The plates are read using UV microscopy and individual wells reported as positive or negative. The Positive Control and Negative Control samples are used to monitor the test system. If the controls are within expected ranges the test results are acceptable in regard to test method parameters. The serum antibody titers are calculated using the highest dilution showing specific IFA reactivity and the number of wells positive per dilution, or a 50% endpoint is calculated using the appropriate Reed-Muench formula.

Example 3

Efficacy of PCV2 ORF-2 (Ingelvac® CircoFLEX™) in Treatment of PRDC

Objective

The purpose of this study was the demonstration of the efficacy of Ingelvac® CircoFLEX in the control of PCV2-associated PRDC.

Study Performance 1542 conventional pigs belonging to three consecutive week groups, each comprising approximately 500 animals, were included into the study. The study animals were blocked by weight and litter assignment and randomly assigned to one group of vaccinates (n=769) and one control group (n=773).

Group 1: At study day 0 the pigs were vaccinated intramusculary at the age of approximately 20 days by a single dose of Ingelvac® CircoFLEX containing PCV2 ORF-2 protein as the active substance with an RP of 1 (per dose of 1 ml) and Carbopol® as adjuvant.

Group 2: The control group received 1 ml of control article which contained PCV2 ORF-2 protein free cell culture supernatant and Carbopol® as adjuvant.

Group 3: Untreated pigs.

The study was terminated at the end of fattening (study week 22).

Parameters Recorded

Parameters recorded were as follows:

Individual body weight (all animals)

Frequency of 'runts' (all animals)

Clinical signs (all animals)

Mortality (all animals)

PCV2 viremia in serum: onset, end, duration of viremia, virus load (17% of study animals)

Necropsy (every dead or euthanized animal, if possible)

Disease Situation at the Farm

According to the disease history of the rearing and fattening farm, animals experienced respiratory symptoms related to the Porcine Respiratory Disease Complex (PRDC) from the middle of fattening onwards. These symptoms were accompanied by a reduced weight gain (ADWG 750-780 g) and an increased mortality rate (5.5-6.6%) during the fattening period. Pathogens that were considered to be involved in PRDC at that time were PCV2, PRRSV, *Pasteurella multocida, Bordetella bronchiseptica* and occasionally SIV. For the course of this study *Mycoplasma hyopneumoniae* and *Mycoplasma hyorhinis* were additionally found to be involved in this disease complex. Interestingly, results from this study give evidence for the fact that both the PRRSV and the *Mycoplasma hyopneumoniae* infection occurred approximately 4-6 weeks before onset of PCV2 viremia. However, as the number of dead animals over the course of the study and the frequency of respiratory symptoms before and after the onset of PCV2 viremia reveal, animals remained rather unaffected from these two infectious pathogens.

Results

Body Weight, Weight Gain, Average Daily Weight Gain

Body weight of the two treatment groups was comparable at the time of study initiation. At study weeks 17 and 22, the body weight of the vaccinated group was significantly higher than the body weight of the placebo-treated group (p=0.0007 and p<0.0001, respectively).

From study initiation until study week 22, vaccinated animals had gained 2.8 kg more weight than placebo-treated animals. This corresponds to a 13 g/d higher ADWG in vaccinated animals from study initiation until study week 17 and an 18 g/d higher ADWG in vaccinated animals until study week 22. For the entire fattening period (study week 7-22), the ADWG could thus be increased from 777 g/d in placebo-treated animals (comparable to historical 750-780 g/d ADWG) to 803 g/d in vaccinated animals (Table 1 and FIG. 1).

TABLE 1

Comparison of Body weight, Weight gain and ADWG (pooled data of all three week groups)

| | Study week | Placebo-treated Group (LSMean) | Vaccinated Group (LSMean) | Difference (IVP-CP) | p-value[1)] |
|---|---|---|---|---|---|
| Live Body Weight | 0 | 6.45 kg | 6.59 kg | 0.14 kg | 0.1289 ns |
| | 7 | 25.79 kg | 26.18 kg | 0.39 kg | 0.3955 ns |
| | 12 | 50.63 kg | 51.01 kg | 0.38 kg | 0.9564 ns |
| | 17 | 78.29 kg | 80.22 kg | 1.93 kg | 0.0007 *** |
| | 22 | 106.55 kg | 109.77 kg | 3.22 kg | <0.0001 *** |
| Weight Gain | 0-17 | 71.97 kg | 73.51 kg | 1.54 kg | 0.0007 *** |
| | 0-22 | 100.22 kg | 103.02 kg | 2.80 kg | <0.0001 *** |
| ADWG | 0-17 | 603 g/d | 616 g/d | 13 g/d | 0.0007 *** |
| | 0-22 | 649 g/d | 667 g/d | 18 g/d | <0.0001 *** |
| | 7-22 | 777 g/d | 803 g/d | 26 g/d | <0.0001 *** |

[1)]p-value of t-test for comparison between groups,
ns: not significant,
*** significant,
$p \leq 0.001$ Viremia in Blood Vaccinated animals showed a slightly later onset of viremia (1.5 days later), a significantly earlier end of viremia (p<0.0001), a significantly shorter duration of viremia (p<0.0001), a significantly lower number of positive sampling days per animal (p<0.0001) and a significant general reduction in the virus load (p<0.0001). The highest proportion of viremic animals was observed at study week 17 with 75% viremic animals in the placebo group and 28% viremic animals in the vaccinated group.

TABLE 2

Comparison of Viremia in Blood (pooled data of all three week groups)

| Study week | Placebo-treated Group (Mean) | Vaccinated Group (Mean) | Difference (CP-IVP) | p-value[2)] |
|---|---|---|---|---|
| Onset of viremia | 104.4 days | 105.9 days | −1.5 days | 0.3244 ns |
| End of viremia | 138.7 days | 123.3 days | 15.4 days | <0.0001 *** |
| Duration of virema | 34.3 days | 17.4 days | 16.9 days | <0.0001 *** |
| Number of positive sampling days | 4.3 days | 1.4 days | 2.9 days | <0.0001 *** |
| Mean Sum gE[1)] (log 10) | 22.7 | 7.1 | 15.6 | <0.0001 *** |

Figure 2:
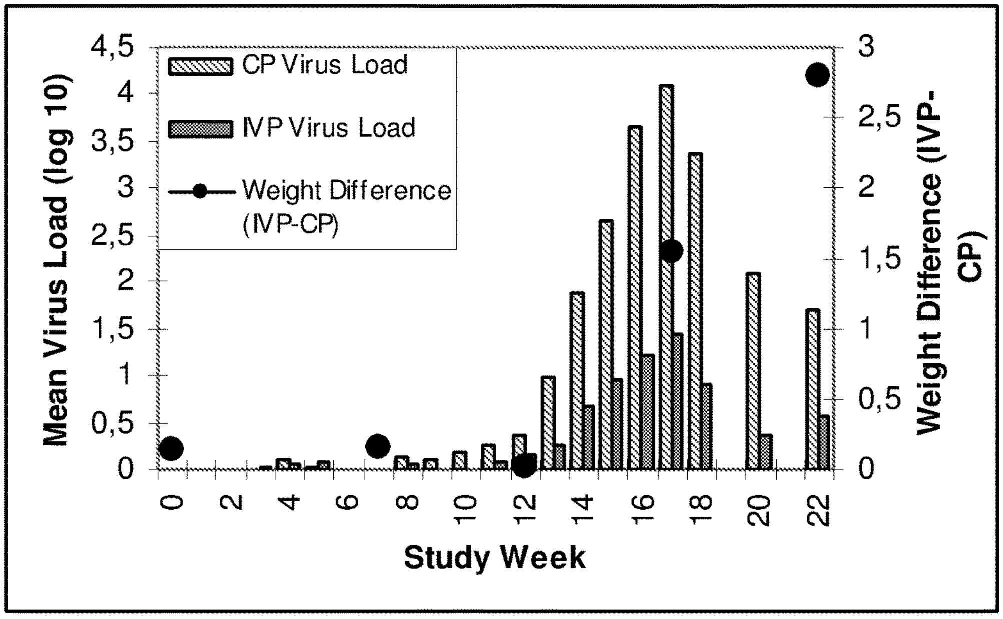
FIG. 2 is a graph illustrating development of the difference in body weight (IVP-CP) and mean virus load (log 10) over the course of the study.

[1)]gE: genomic equivalents per ml
[2)]p-value (of the Wilcoxon Mann-whitney test for comparison between groups),
ns: not significant,
*** significant,
$p \leq 0.001$ Correlation of Viremia in Blood with Body Weight FIG. 2 illustrates the virus load in sample animals of both treatment groups over the course of the study compared to the difference in live body weight (CP-IVP) of all animals from both treatment groups on the respective weighing time points. When comparing the curves for body weight difference with the bars representing the virus load, it becomes obvious that the observed differences in body weight between both treatment groups (study weeks 17 and 22) occur after the onset of viremia (study week 14-16). While the virus load is decreasing after a peak at study week 17, the difference in body weight between groups is further increasing until the end of fattening. Together these data give evidence for a correlation between the observed higher body weight gain development at study weeks 17 and 22 in the vaccinated group and the onset, duration and level of viremia.

Calculation of the Spearman rank coefficient confirmed the existence of a statistical significant correlation between viremia and the difference in weight gain development in placebo-treated animals at study weeks 17 and 22. A low body weight in placebo-treated animals was correlated with an early onset, a long duration of viremia and a high virus load. For vaccinated animals no such correlation could be found indicating that the higher body weight in the vaccinated animals was the result of a delayed onset and shorter duration of viremia as well as of a lower virus load in blood.

Frequency of Runts

No significant differences in the frequency of ‘runts’ could be observed between the vaccinated and the placebo-treated group on any of the respective weighing time points. After the onset of PCV2 viremia (study week 14-16), the frequency of ‘runts’ was generally low in both treatment groups (2.2-3.9%).

TABLE 3

Comparison of the frequency of ‘runts’ (pooled data of all three week groups)

| | Before Onset of viremia | | | After onset of viremia | |
|---|---|---|---|---|---|
| Study week | 0 | 7 | 12 | 17 | 22 |
| CP | 17.08% | 11.16% | 5.02% | 3.57% | 2.97% |
| IVP | 17.17% | 11.03% | 5.32% | 3.99% | 2.23% |
| P | 1.0000 | 0.6845 | 0.8147 | 0.6830 | 0.4082 |

P: p-value of t-test for comparison between groups;
$p > 0.05$ no significant

Clinical Signs

Before onset of viremia predominant clinical signs were lamenesses, cough and diarrhea (in 8-12% of animals). They occurred with equal frequency in both treatment groups. Upon necropsy of dead animals and subsequent microbiological examination *Streptococcus suis* was identified as a possible infectious pathogen for lamenesses, *Haemophilus parasuis* and *Bordetella bronchiseptica* were identified as possible infectious pathogens for cough, and haemolytic *E. coli* was identified as a possible reason for diarrhea.

After the onset of viremia, the predominant clinical symptoms observed in animals of both treatment groups were cough and lamenesses. Serological periodic analyses for other infectious pathogens and microbiological findings upon necropsy revealed that PCV2 viremia was accompanied by a (preceding) PRRSV and *Mycoplasma hyopneumoniae* infection. Together with PCV2, these infectious pathogens form part of PRDC which is considered to be the cause for the increased frequency of coughing animals after the onset of viremia. Compared to the placebo-treated animals, the frequency of cough and dyspnea in vaccinated animals was reduced by 12.2% and 17.5%, respectively. These findings are however without any statistical significance. The increased frequency of lamenesses after the onset of viremia compared to the time before onset of viremia is most likely caused by chronic forms of *Streptococcus suis*, arthritis, or by weaknesses of the joint apparatus and these affected both treatment groups in the same way (p=0.8321). Similarly, the frequency of other clinical findings (diarrhea, skin abnormalities, behaviour) after the onset of viremia was almost equal between the two treatment groups.

Mortality

Before onset of viremia the mortality rate was comparable in both treatment groups (vaccinated animals: 5.20%, placebo-treated animals: 5.17%). After the onset of viremia placebo-treated animals had a significant higher mortality rate than vaccinated animals (vaccinated animals: 1.51%, placebo-treated animals: 3.68%, p=0.0127). Compared to placebo-treated animals, the mortality rate in vaccinated animals was reduced by 59%.

CONCLUSION

The study has been conducted on a farm that showed typical symptoms of PRDC at the late phase of fattening. At the age of 17 to 19 weeks, pigs developed respiratory symptoms, an increased mortality rate, and a loss of weight gain. Upon serological and microbiological screening PCV2, PRRSV, *Mycoplasma hyopneumoniae, Mycoplasma hyorhinis* and *Pasteurella multocida* were identified as possible pathogens being involved in this disease complex.

Compared to the placebo-treated control group the following statistically significant findings were noted for the vaccinated group:

- reduction of loss of weight gain
- reduction of mortality
- reduction of the duration of viremia and earlier end of viremia
- reduction of the virus load
- reduction of cough and dyspnea As expected, no statistically significant differences could be observed with regard to the frequency of ‘runts’ since the occurrence of ‘runts’ is not a typical finding for PRDC.

Together these findings allow the following conclusions:

1. The study has been conducted in a herd that got affected with PRDC at the middle to late phase of fattening. PCV2 was clearly involved in this disease complex since respiratory symptoms, loss of weight gain and an increase in mortality was only observed after the onset of viremia.
2. Vaccination of animals with Ingelvac® CircoFLEX™ could reduce or even prevent clinically relevant parameters that are related to PCV2 associated PRDC

What is claimed is:

1. A method for the prophylaxis or treatment of:

a) porcine respiratory disease complex (PRDC); or b) one or more clinical signs of PRDC selected from the group consisting of cough, dyspnea, slow growth, decreased feed efficiency, lethargy, anorexia, and/or a marked increase in mortality in the middle to late phase of fattening, wherein said PRDC is caused by PCV2 and at least one other PRDC causing pathogen, the method comprising the step of administering a single dose of a therapeutically effective amount of recombinant PCV2 ORF2 protein or an immunogenic composition comprising a single dose of recombinant PCV2 ORF2 protein to a porcine between 1 and 22 days of age at the time of administration, wherein the therapeutically effective amount of recombinant PCV2 ORF2 protein comprises about 4 μg to 400 μg of recombinant PCV2 ORF2 protein, and wherein the recombinant PCV2 ORF2 protein is a polypeptide selected from the group consisting of:

i. a polypeptide comprising the sequence of SEQ ID NO: 5, SEQ ID NO: 6, or SEQ ID NO: 11;

ii. a polypeptide that is at least 90% homologous to the polypeptide of i), iii. a polypeptide that is encoded by a DNA comprising the sequence of SEQ ID NO: 3 or SEQ ID NO: 4; and iv. a polypeptide that is encoded by a polynucleotide that is at least 90% homologous to the polynucleotide of iii).

2. The method according to claim 1, wherein the cough and dyspnea, are refractory to antibiotic therapy.

3. The method according to claim 1, wherein the porcine belongs to a herd that is positive for PCV2.

4. The method according to claim 1, wherein the porcine belongs to a herd that is positive for PCV2 and one or more further pathogen(s) selected from the group consisting of PRRSV, *Mycoplasma hyopneumoniae, Bordetella bronchiseptica*, Swine influenza virus, *Mycoplasma hyorhinis, Streptococcus suis* and/or *Pasteurella multocida.*

5. The method according to claim 1, wherein the porcine belongs to a farm that is positive for PCV2 and one or more further pathogen(s) selected from the group consisting of PRRSV, *Mycoplasma hyopneumoniae, Bordetella bronchiseptica*, Swine influenza virus, *Mycoplasma hyorhinis, Streptococcus suis* and/or *Pasteurella multocida.*

6. The method according to claim 1, wherein the PCV2 protein is a recombinant baculovirus expressed ORF2 protein of PCV2.

7. The method of claim 1, wherein the therapeutically effective amount of recombinant PCV2 ORF2 protein is about 4 μg to 100 μg.

8. The method of claim 1, wherein the therapeutically effective amount of recombinant PCV2 ORF2 protein is about 4 μg to 50 μg.

9. The method of claim 1, wherein the therapeutically effective amount of recombinant PCV2 ORF2 protein is about 4 μg to 16 μg.

10. The method of claim 1, wherein the recombinant PCV2 ORF2 protein is substantially purified.

11. The method of claim 1, wherein the prophylaxis or treatment of one or more clinical signs of PRDC occurs after the therapeutically effective amount of recombinant PCV2

ORF2 protein or immunogenic composition comprising recombinant PCV2 ORF2 protein is administered.

12. A method for the prophylaxis or treatment of:

a) porcine respiratory disease complex (PRDC); or b) one or more clinical signs of PRDC selected from the group consisting of cough, dyspnea, slow growth, decreased feed efficiency, lethargy, anorexia, and/or a marked increase in mortality in the middle to late phase of fattening in a porcine between 16 and 22 weeks of age, wherein said PRDC is caused by PCV2 and at least one other PRDC causing pathogen, wherein the porcine is between 1 and 22 days of age at the time of administration, wherein the method comprises administering a single dose to a porcine a therapeutically effective amount of a recombinant PCV2 ORF2 protein or an immunogenic composition comprising a recombinant PCV2 ORF2 protein, wherein the therapeutically effective amount of recombinant PCV2 ORF2 protein comprises about 4 μg to 400 μg of recombinant PCV2 ORF2 protein, and wherein the recombinant PCV2 ORF2 protein is a polypeptide selected from the group consisting of:

i. a polypeptide comprising the sequence of SEQ ID NO: 5, SEQ ID NO: 6, or SEQ ID NO: 11;

ii. a polypeptide that is at least 90% homologous to the polypeptide of i), iii. a polypeptide that is encoded by a DNA comprising the sequence of SEQ ID NO: 3 or SEQ ID NO: 4; and iv. a polypeptide that is encoded by a polynucleotide that is at least 90% homologous to the polynucleotide of iii).

13. The method according to claim 12, wherein the cough and dyspnea, are refractory to antibiotic therapy.

14. The method according to claim 12, wherein the porcine belongs to a herd that is positive for PCV2.

15. The method according to claim 12, wherein the PCV2 protein is a recombinant baculovirus expressed ORF2 protein of PCV2.

16. The method of claim 12, wherein the therapeutically effective amount of recombinant PCV2 ORF2 protein is about 4 μg to 100 μg.

17. A method for the prophylaxis or treatment of:

a) porcine respiratory disease complex (PRDC) or b) one or more clinical signs of PRDC selected from the group consisting of cough, dyspnea, slow growth, decreased feed efficiency, lethargy, anorexia, and/or a marked increase in mortality in the middle to late phase of fattening, wherein said PRDC is caused by PCV2 and at least one other PRDC causing pathogen, the method comprising the step of administering a therapeutically effective amount of a single dose of a recombinant PCV2 ORF2 protein or an immunogenic composition comprising a recombinant PCV2 ORF2 protein to a porcine, wherein the administration of the single dose is effective for the vaccination of a porcine between 1 and 22 days of age against PCV2 infection, wherein the therapeutically effective amount of a recombinant PCV2 ORF2 protein or immunogenic composition comprising a recombinant PCV2 ORF2 protein comprises about 4 μg to 400 μg of recombinant PCV2 ORF2 protein, and wherein the recombinant PCV2 ORF2 protein is a polypeptide selected from the group consisting of:

i. a polypeptide comprising the sequence of SEQ ID NO: 5, SEQ ID NO: 6, or SEQ ID NO: 11;

ii. a polypeptide that is at least 90% homologous to the polypeptide of i), iii. a polypeptide that is encoded by a DNA comprising the sequence of SEQ ID NO: 3 or SEQ ID NO: 4; and iv. a polypeptide that is encoded by a polynucleotide that is at least 90% homologous to the polynucleotide of iii).

18. The method according to claim 17, wherein the cough and dyspnea, are refractory to antibiotic therapy.

19. The method according to claim 17, wherein the porcine belongs to a herd that is positive for PCV2.

20. The method according to claim 17, wherein the porcine belongs to a herd that is positive for PCV2 and one or more further pathogen(s) selected from the group consisting of PRRSV, *Mycoplasma hyopneumoniae, Bordetella bronchiseptica*, Swine influenza virus, *Mycoplasma hyorhinis, Streptococcus suis* and/or *Pasteurella multocida.*

21. The method according to claim 17, wherein the porcine belongs to a farm that is positive for PCV2 and one or more further pathogen(s) selected from the group consisting of PRRSV, *Mycoplasma hyopneumoniae, Bordetella bronchiseptica*, Swine influenza virus, *Mycoplasma hyorhinis, Streptococcus suis* and/or *Pasteurella multocida.*

22. The method according to claim 17, wherein the PCV2 protein is a recombinant baculovirus expressed ORF2 protein of PCV2.

23. The method of claim 17, wherein the therapeutically effective amount of recombinant PCV2 ORF2 protein is about 4 μg to 100 μg.

24. The method of claim 17, wherein the therapeutically effective amount of recombinant PCV2 ORF2 protein is about 4 μg to 50 μg.

25. The method of claim 17, wherein the therapeutically effective amount of recombinant PCV2 ORF2 protein is about 4 μg to 16 μg.

26. The method of claim 17, wherein the recombinant PCV2 ORF2 protein is substantially purified.

27. The method of claim 17, wherein the prophylaxis or treatment of one or more clinical signs of PRDC occurs after the therapeutically effective amount of recombinant PCV2 ORF2 protein or immunogenic composition comprising recombinant PCV2 ORF2 protein is administered.

28. A method for the prophylaxis or treatment of:

a) porcine respiratory disease complex (PRDC) or b) one or more clinical signs of PRDC selected from the group consisting of cough, dyspnea, slow growth, decreased feed efficiency, lethargy, anorexia, and/or a marked increase in mortality in the middle to late phase of fattening in a porcine between 16 and 22 weeks of age, wherein said PRDC is caused by PCV2 and at least one other PRDC causing pathogen, the method comprising the step of administering a therapeutically effective amount of a single dose of a recombinant PCV2 ORF2 protein or an immunogenic composition comprising a recombinant PCV2 ORF2 protein to a porcine, wherein the administration of the single dose is effective for the vaccination of a porcine between 1 and 22 days of age against PCV2 infection, wherein the therapeutically effective amount of a recombinant PCV2 ORF2 protein or immunogenic composition comprising a recombinant PCV2 ORF2 protein comprises about 4 μg to 400 μg of recombinant PCV2 ORF2 protein, and wherein the recombinant PCV2 ORF2 protein is a polypeptide selected from the group consisting of:

i. a polypeptide comprising the sequence of SEQ ID NO: 5, SEQ ID NO: 6, or SEQ ID NO: 11;

ii. a polypeptide that is at least 90% homologous to the polypeptide of i), iii. a polypeptide that is encoded by a DNA comprising the sequence of SEQ ID NO: 3 or SEQ ID NO: 4; and iv. a polypeptide that is encoded by a polynucleotide that is at least 90% homologous to the polynucleotide of iii).

29. The method according to claim 28, wherein the cough and dyspnea, are refractory to antibiotic therapy.

30. The method according to claim 28, wherein the porcine belongs to a herd that is positive for PCV2.

31. The method according to claim 28, wherein the PCV2 protein is a recombinant baculovirus expressed ORF2 protein of PCV2.

* * * * *

SEQUENCE LISTING

```
<160> NUMBER OF SEQ ID NOS: 11

<210> SEQ ID NO 1
<211> LENGTH: 8
<212> TYPE: DNA
```

-continued

<213> ORGANISM: Artificial Sequence
<220> FEATURE:
<223> OTHER INFORMATION: This is a modified Kozak's sequence.

<400> SEQUENCE: 1 ccgccatg 8

<210> SEQ ID NO 2
<211> LENGTH: 6
<212> TYPE: DNA
<213> ORGANISM: Artificial Sequence
<220> FEATURE:
<223> OTHER INFORMATION: This is a recombinant Eco R1 sequence.

<400> SEQUENCE: 2 gaattc 6

<210> SEQ ID NO 3
<211> LENGTH: 713
<212> TYPE: DNA
<213> ORGANISM: Porcine circovirus

<400> SEQUENCE: 3
cagctatgac gtatccaagg aggcgttacc gcagaagaag acaccgcccc cgcagccatc 60
ttggccagat cctccgccgc cgcccctggc tcgtccaccc ccgccaccgc taccgttgga 120
gaaggaaaaa tggcatcttc aacacccgcc tctcccgcac cttcggatat actgtggaga 180
aggaaaaatg gcatcttcaa cacccgcctc tcccgcacct tcggatatac tgtgacgact 240
ttgttccccc gggagggggg accaacaaaa tctctatacc ctttgaatac tacagaataa 300
gaaaggttaa ggttgaattc tggccctgct cccccatcac ccagggtgat aggggagtgg 360
gctccactgc tgttattcta gatgataact ttgtaacaaa ggccacagcc ctaacctatg 420
acccatatgt aaactactcc tcccgccata caatccccca acccttctcc taccactccc 480
gttacttcac acccaaacct gttcttgact ccactattga ttacttccaa ccaaataaca 540
aaaggaatca gctttggctg aggctacaaa cctctagaaa tgtggaccac gtaggcctcg 600
gcactgcgtt cgaaaacagt aaatacgacc aggactacaa tatccgtgta accatgtatg 660
tacaattcag agaatttaat cttaaagacc ccccacttaa accctaaatg aat 713

<210> SEQ ID NO 4
<211> LENGTH: 713
<212> TYPE: DNA
<213> ORGANISM: Porcine circovirus

<400> SEQUENCE: 4
ccgccatgac gtatccaagg aggcgttacc gcagaagaag acaccgcccc cgcagccatc 60
ttggccagat cctccgccgc cgcccctggc tcgtccaccc ccgccaccgc taccgttgga 120
gaaggaaaaa tggcatcttc aacacccgcc tctcccgcac cttcggatat actgtcaagg 180
ctaccacagt cacaacgccc tcctgggcgg tggacatgat gagatttaat attgacgact 240
ttgttccccc gggagggggg accaacaaaa tctctatacc ctttgaatac tacagaataa 300
gaaaggttaa ggttgaattc tggccctgct cccccatcac ccagggtgat aggggagtgg 360
gctccactgc tgttattcta gatgataact ttgtaacaaa ggccacagcc ctaacctatg 420
acccatatgt aaactactcc tcccgccata caatccccca acccttctcc taccactccc 480
gttacttcac acccaaacct gttcttgact ccactattga ttacttccaa ccaaataaca 540
aaaggaatca gctttggctg aggctacaaa cctctagaaa tgtggaccac gtaggcctcg 600

```
gcactgcgtt cgaaaacagt aaatacgacc aggactacaa tatccgtgta accatgtatg    660

tacaattcag agaatttaat cttaaagacc ccccacttga accctaagaa ttc           713


<210> SEQ ID NO 5
<211> LENGTH: 233
<212> TYPE: PRT
<213> ORGANISM: Porcine circovirus

<400> SEQUENCE: 5

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230


<210> SEQ ID NO 6
<211> LENGTH: 233
<212> TYPE: PRT
<213> ORGANISM: Porcine circovirus

<400> SEQUENCE: 6

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
```

-continued

```
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230
```

<210> SEQ ID NO 7
<211> LENGTH: 756
<212> TYPE: DNA
<213> ORGANISM: Artificial Sequence
<220> FEATURE:
<223> OTHER INFORMATION: This sequence is from porcine circovirus type 2, open reading frame 2, together with a portion from the pGEM T-easy vector.

<400> SEQUENCE: 7

```
gcggccgcgg gaattcgatc cgccatgacg tatccaagga ggcgttaccg cagaagaaga     60

caccgccccc gcagccatct tggccagatc ctccgccgcc gcccctggct cgtccacccc    120

cgccaccgct accgttggag aaggaaaaat ggcatcttca acacccgcct ctcccgcacc    180

ttcggatata ctgtcaaggc taccacagtc acaacgccct cctgggcggt ggacatgatg    240

agatttaata ttgacgactt tgttcccccg ggagggggga ccaacaaaat ctctataccc    300

tttgaatact acagaataag aaaggttaag gttgaattct ggccctgctc ccccatcacc    360

cagggtgata ggggagtggg ctccactgct gttattctag atgataactt tgtaacaaag    420

gccacagccc taacctatga cccatatgta aactactcct cccgccatac aatcccccaa    480

cccttctcct accactcccg ttacttcaca cccaaacctg ttcttgactc cactattgat    540

tacttccaac caaataacaa aaggaatcag ctttggctga ggctacaaac ctctagaaat    600

gtggaccacg taggcctcgg cactgcgttc gaaaacagta aatacgacca ggactacaat    660

atccgtgtaa ccatgtatgt acaattcaga gaatttaatc ttaaagaccc cccacttgaa    720

ccctaagaat tctatcacta gtgaattcgc ggccgc                              756
```

<210> SEQ ID NO 8
<211> LENGTH: 10387
<212> TYPE: DNA
<213> ORGANISM: Artificial Sequence
<220> FEATURE:
<223> OTHER INFORMATION: This is the porcine circovirus type 2, ORF-2construct, which includes baculovirus and pGEM T-easy coding sequences.

-continued

<400> SEQUENCE: 8

```
aagctttact cgtaaagcga gttgaaggat catatttagt tgcgtttatg agataagatt     60
gaaagcacgt gtaaaatgtt tcccgcgcgt tggcacaact atttacaatg cggccaagtt    120
ataaaagatt ctaatctgat atgttttaaa acacctttgc ggcccgagtt gtttgcgtac    180
gtgactagcg aagaagatgt gtggaccgca gaacagatag taaaacaaaa ccctagtatt    240
ggagcaataa tcgatttaac caacacgtct aaatattatg atggtgtgca tttttttgcgg   300
gcgggcctgt tatacaaaaa aattcaagta cctggccaga ctttgccgcc tgaaagcata    360
gttcaagaat ttattgacac ggtaaaagaa tttacagaaa agtgtcccgg catgttggtg    420
ggcgtgcact gcacacacgg tattaatcgc accggttaca tggtgtgcag atatttaatg    480
cacaccctgg gtattgcgcc gcaggaagcc atagatagat tcgaaaaagc cagaggtcac    540
aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg gatattctcc accacaatgt tggcaacgtt gatgttacgt ttatgctttt    780
ggttttccac gtacgtcttt tggccggtaa tagccgtaaa cgtagtgccg tcgcgcgtca    840
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680
tatgggggaa catgcgccgc tacaacactc gtcgttatga acgcagacgg cgccggtctc   1740
ggcgcaagcg gctaaaacgt gttgcgcgtt caacgcggca aacatcgcaa aagccaatag   1800
tacagttttg atttgcatat taacggcgat tttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
```

-continued gcgcgtattt taacaaacta gccatcttgt aagttagttt catttaatgc aactttatcc 2340
aataatatat tatgtatcgc acgtcaagaa ttaacaatgc gcccgttgtc gcatctcaac 2400
acgactatga tagagatcaa ataaagcgcg aattaaatag cttgcgacgc aacgtgcacg 2460
atctgtgcac gcgttccggc acgagctttg attgtaataa gtttttacga agcgatgaca 2520
tgacccccgt agtgacaacg atcacgccca aaagaactgc cgactacaaa attaccgagt 2580
atgtcggtga cgttaaaact attaagccat ccaatcgacc gttagtcgaa tcaggaccgc 2640
tggtgcgaga agccgcgaag tatggcgaat gcatcgtata acgtgtggag tccgctcatt 2700
agagcgtcat gtttagacaa gaaagctaca tatttaattg atcccgatga ttttattgat 2760
aaattgaccc taactccata cacggtattc tacaatggcg gggttttggt caaaatttcc 2820
ggactgcgat tgtacatgct gttaacggct ccgcccacta ttaatgaaat taaaaattcc 2880
aattttaaaa aacgcagcaa gagaaacatt tgtatgaaag aatgcgtaga aggaaagaaa 2940
aatgtcgtcg acatgctgaa caacaagatt aatatgcctc cgtgtataaa aaaaatattg 3000
aacgatttga aagaaaacaa tgtaccgcgc ggcggtatgt acaggaagag gtttatacta 3060
aactgttaca ttgcaaacgt ggtttcgtgt gccaagtgtg aaaaccgatg tttaatcaag 3120
gctctgacgc atttctacaa ccacgactcc aagtgtgtgg gtgaagtcat gcatctttta 3180
atcaaatccc aagatgtgta taaaccacca aactgccaaa aaatgaaaac tgtcgacaag 3240
ctctgtccgt ttgctggcaa ctgcaagggt ctcaatccta tttgtaatta ttgaataata 3300
aaacaattat aaatgctaaa tttgtttttt attaacgata caaaccaaac gcaacaagaa 3360
catttgtagt attatctata attgaaaacg cgtagttata atcgctgagg taatatttaa 3420
aatcattttc aaatgattca cagttaattt gcgacaatat aattttattt tcacataaac 3480
tagacgcctt gtcgtcttct tcttcgtatt ccttctcttt ttcatttttc tcctcataaa 3540
aattaacata gttattatcg tatccatata tgtatctatc gtatagagta aatttttttgt 3600 tgtcataaat atatatgtct tttttaatgg ggtgtatagt accgctgcgc atagtttttc 3660
tgtaatttac aacagtgcta ttttctggta gttcttcgga gtgtgttgct ttaattatta 3720
aatttatata atcaatgaat ttgggatcgt cggttttgta caatatgttg ccggcatagt 3780
acgcagcttc ttctagttca attacaccat tttttagcag caccggatta acataacttt 3840
ccaaaatgtt gtacgaaccg ttaaacaaaa acagttcacc tcccttttct atactattgt 3900
ctgcgagcag ttgtttgttg ttaaaaataa cagccattgt aatgagacgc acaaactaat 3960
atcacaaact ggaaatgtct atcaatatat agttgctgat atcatggaga taattaaaat 4020
gataaccatc tcgcaaataa ataagtattt tactgttttc gtaacagttt tgtaataaaa 4080
aaacctataa atattccgga ttattcatac cgtcccacca tcgggcgcgg atcagatctg 4140
cagcggccgc gggaattcga tccgccatga cgtatccaag gaggcgttac cgcagaagaa 4200
gacaccgccc ccgcagccat cttggccaga tcctccgccg ccgcccctgg ctcgtccacc 4260
cccgccaccg ctaccgttgg agaaggaaaa atggcatctt caacacccgc ctctcccgca 4320
ccttcggata tactgtcaag gctaccacag tcacaacgcc ctcctgggcg gtggacatga 4380
tgagatttaa tattgacgac tttgttcccc cgggaggggg gaccaacaaa atctctatac 4440
cctttgaata ctacagaata agaaaggtta aggttgaatt ctggccctgc tcccccatca 4500
cccagggtga taggggagtg ggctccactg ctgttattct agatgataac tttgtaacaa 4560
aggccacagc cctaacctat gacccatatg taaactactc ctcccgccat acaatccccc 4620
aacccttctc ctaccactcc cgttacttca cacccaaacc tgttcttgac tccactattg 4680

-continued

```
attacttcca accaaataac aaaaggaatc agctttggct gaggctacaa acctctagaa   4740
atgtggacca cgtaggcctc ggcactgcgt tcgaaaacag taaatacgac caggactaca   4800
atatccgtgt aaccatgtat gtacaattca gagaatttaa tcttaaagac cccccacttg   4860
aaccctaaga attctatcac tagtgaattc gcggccgccg gccgctccag aattctagaa   4920
ggtacccggg atcctttcct gggacccggc aagaaccaaa aactcactct cttcaaggaa   4980
atccgtaatg ttaaacccga cacgatgaag cttgtcgttg gatggaaagg aaaagagttc   5040
tacagggaaa cttggacccg cttcatggaa gacagcttcc ccattgttaa cgaccaagaa   5100
gtgatggatg ttttccttgt tgtcaacatg cgtcccacta gacccaaccg ttgttacaaa   5160
ttcctggccc aacacgctct gcgttgcgac cccgactatg tacctcatga cgtgattagg   5220
atcgtcgagc cttcatgggt gggcagcaac aacgagtacc gcatcagcct ggctaagaag   5280
ggcggcggct gcccaataat gaaccttcac tctgagtaca ccaactcgtt cgaacagttc   5340
atcgatcgtg tcatctggga gaacttctac aagcccatcg tttacatcgg taccgactct   5400
gctgaagagg aggaaattct ccttgaagtt tccctggtgt tcaaagtaaa ggagtttgca   5460
ccagacgcac ctctgttcac tggtccggcg tattaaaaca cgatacattg ttattagtac   5520
atttattaag cgctagattc tgtgcgttgt tgatttacag acaattgttg tacgtatttt   5580
aataattcat taaatttata atctttaggg tggtatgtta gagcgaaaat caaatgattt   5640
tcagcgtctt tatatctgaa tttaaatatt aaatcctcaa tagatttgta aaataggttt   5700
cgattagttt caaacaaggg ttgtttttcc gaaccgatgg ctggactatc taatggattt   5760
tcgctcaacg ccacaaaact tgccaaatct tgtagcagca atctagcttt gtcgatattc   5820
gtttgtgttt tgttttgtaa taaaggttcg acgtcgttca aaatattatg cgcttttgta   5880
tttctttcat cactgtcgtt agtgtacaat tgactcgacg taaacacgtt aaataaagct   5940
tggacatatt taacatcggg cgtgttagct ttattaggcc gattatcgtc gtcgtcccaa   6000
ccctcgtcgt tagaagttgc ttccgaagac gattttgcca tagccacacg acgcctatta   6060
attgtgtcgg ctaacacgtc cgcgatcaaa tttgtagttg agctttttgg aattatttct   6120
gattgcgggc gtttttgggc gggtttcaat ctaactgtgc ccgattttaa ttcagacaac   6180
acgttagaaa gcgatggtgc aggcggtggt aacatttcag acggcaaatc tactaatggc   6240
ggcggtggtg gagctgatga taaatctacc atcggtggag gcgcaggcgg ggctggcggc   6300
ggaggcggag gcggaggtgg tggcggtgat gcagacggcg gtttaggctc aaatgtctct   6360
ttaggcaaca cagtcggcac ctcaactatt gtactggttt cgggcgccgt tttggtttg    6420
accggtctga gacgagtgcg atttttttcg tttctaatag cttccaacaa ttgttgtctg   6480
tcgtctaaag gtgcagcggg ttgaggttcc gtcggcattg gtggagcggg cggcaattca   6540
gacatcgatg gtggtggtgg tggtggaggc gctggaatgt taggcacggg agaaggtggt   6600
ggcggcggtg ccgccggtat aatttgttct ggtttagttt gttcgcgcac gattgtgggc   6660
accggcgcag gcgccgctgg ctgcacaacg gaaggtcgtc tgcttcgagg cagcgcttgg   6720
ggtggtggca attcaatatt ataattggaa tacaaatcgt aaaaatctgc tataagcatt   6780
gtaatttcgc tatcgtttac cgtgccgata tttaacaacc gctcaatgta agcaattgta   6840
ttgtaaagag attgtctcaa gctcgccgca cgccgataac aagccttttc atttttacta   6900
cagcattgta gtggcgagac acttcgctgt cgtcgacgta catgtatgct ttgttgtcaa   6960
aaacgtcgtt ggcaagcttt aaaatattta aaagaacatc tctgttcagc accactgtgt   7020
```

-continued

```
tgtcgtaaat gttgtttttg ataatttgcg cttccgcagt atcgacacgt tcaaaaaatt   7080
gatgcgcatc aattttgttg ttcctattat tgaataaata agattgtaca gattcatatc   7140
tacgattcgt catggccacc acaaatgcta cgctgcaaac gctggtacaa ttttacgaaa   7200
actgcaaaaa cgtcaaaact cggtataaaa taatcaacgg gcgctttggc aaaatatcta   7260
ttttatcgca caagcccact agcaaattgt atttgcagaa aacaatttcg gcgcacaatt   7320
ttaacgctga cgaaataaaa gttcaccagt taatgagcga ccacccaaat tttataaaaa   7380
tctattttaa tcacggttcc atcaacaacc aagtgatcgt gatggactac attgactgtc   7440
ccgatttatt tgaaacacta caaattaaag gcgagctttc gtaccaactt gttagcaata   7500
ttattagaca gctgtgtgaa gcgctcaacg atttgcacaa gcacaatttc atacacaacg   7560
acataaaact cgaaaatgtc ttatatttcg aagcacttga tcgcgtgtat gtttgcgatt   7620
acggattgtg caaacacgaa aactcactta gcgtgcacga cggcacgttg gagtatttta   7680
gtccggaaaa aattcgacac acaactatgc acgtttcgtt tgactggtac gcggcgtgtt   7740
aacatacaag ttgctaacgt aatcatggtc atagctgttt cctgtgtgaa attgttatcc   7800
gctcacaatt ccacacaaca tacgagccgg aagcataaag tgtaaagcct ggggtgccta   7860
atgagtgagc taactcacat taattgcgtt gcgctcactg cccgctttcc agtcgggaaa   7920
cctgtcgtgc cagctgcatt aatgaatcgg ccaacgcgcg gggagaggcg gtttgcgtat   7980
tgggcgctct tccgcttcct cgctcactga ctcgctgcgc tcggtcgttc ggctgcggcg   8040
agcggtatca gctcactcaa aggcggtaat acggttatcc acagaatcag gggataacgc   8100
aggaaagaac atgtgagcaa aaggccagca aaaggccagg aaccgtaaaa aggccgcgtt   8160
gctggcgttt ttccataggc tccgcccccc tgacgagcat cacaaaaatc gacgctcaag   8220
tcagaggtgg cgaaacccga caggactata aagataccag gcgtttcccc ctggaagctc   8280
cctcgtgcgc tctcctgttc cgaccctgcc gcttaccgga tacctgtccg cctttctccc   8340
ttcgggaagc gtggcgcttt ctcatagctc acgctgtagg tatctcagtt cggtgtaggt   8400
cgttcgctcc aagctgggct gtgtgcacga accccccgtt cagcccgacc gctgcgcctt   8460
atccggtaac tatcgtcttg agtccaaccc ggtaagacac gacttatcgc cactggcagc   8520
agccactggt aacaggatta gcagagcgag gtatgtaggc ggtgctacag agttcttgaa   8580
gtggtggcct aactacggct acactagaag gacagtattt ggtatctgcg ctctgctgaa   8640
gccagttacc ttcggaaaaa gagttggtag ctcttgatcc ggcaaacaaa ccaccgctgg   8700
tagcggtggt ttttttgttt gcaagcagca gattacgcgc agaaaaaaag gatctcaaga   8760
agatcctttg atcttttcta cggggtctga cgctcagtgg aacgaaaact cacgttaagg   8820
gattttggtc atgagattat caaaaaggat cttcacctag atccttttaa attaaaaatg   8880
aagttttaaa tcaatctaaa gtatatatga gtaaacttgg tctgacagtt accaatgctt   8940
aatcagtgag gcacctatct cagcgatctg tctatttcgt tcatccatag ttgcctgact   9000
ccccgtcgtg tagataacta cgatacggga gggcttacca tctggcccca gtgctgcaat   9060
gataccgcga gacccacgct caccggctcc agatttatca gcaataaacc agccagccgg   9120
aagggccgag cgcagaagtg gtcctgcaac tttatccgcc tccatccagt ctattaattg   9180
ttgccgggaa gctagagtaa gtagttcgcc agttaatagt ttgcgcaacg ttgttgccat   9240
tgctacaggc atcgtggtgt cacgctcgtc gtttggtatg gcttcattca gctccggttc   9300
ccaacgatca aggcgagtta catgatcccc catgttgtgc aaaaaagcgg ttagctcctt   9360
cggtcctccg atcgttgtca gaagtaagtt ggccgcagtg ttatcactca tggttatggc   9420
```

-continued

```
agcactgcat aattctctta ctgtcatgcc atccgtaaga tgcttttctg tgactggtga   9480

gtactcaacc aagtcattct gagaatagtg tatgcggcga ccgagttgct cttgcccggc   9540

gtcaatacgg gataataccg cgccacatag cagaacttta aaagtgctca tcattggaaa   9600

acgttcttcg gggcgaaaac tctcaaggat cttaccgctg ttgagatcca gttcgatgta   9660

acccactcgt gcacccaact gatcttcagc atcttttact ttcaccagcg tttctgggtg   9720

agcaaaaaca ggaaggcaaa atgccgcaaa aaagggaata agggcgacac ggaaatgttg   9780

aatactcata ctcttccttt ttcaatatta ttgaagcatt tatcagggtt attgtctcat   9840

gagcggatac atatttgaat gtatttagaa aaataaacaa ataggggttc cgcgcacatt   9900

tccccgaaaa gtgccacctg acgtctaaga aaccattatt atcatgacat taacctataa   9960

aaataggcgt atcacgaggc cctttcgtct cgcgcgtttc ggtgatgacg gtgaaaacct  10020

ctgacacatg cagctcccgg agacggtcac agcttgtctg taagcggatg ccgggagcag  10080

acaagcccgt cagggcgcgt cagcgggtgt tggcgggtgt cggggctggc ttaactatgc  10140

ggcatcagag cagattgtac tgagagtgca ccatatgcgg tgtgaaatac cgcacagatg  10200

cgtaaggaga aaataccgca tcaggcgcca ttcgccattc aggctgcgca actgttggga  10260

agggcgatcg gtgcgggcct cttcgctatt acgccagctg gcgaaagggg gatgtgctgc  10320

aaggcgatta agttgggtaa cgccagggtt ttcccagtca cgacgttgta aaacgacggc  10380

cagtgcc                                                           10387


<210> SEQ ID NO 9
<211> LENGTH: 20
<212> TYPE: PRT
<213> ORGANISM: Porcine circovirus

<400> SEQUENCE: 9

Ser Tyr Pro Arg Arg Arg Tyr Arg Arg Arg Arg His His Pro Pro Ser
1               5                   10                  15

His Leu Gly Gln
            20


<210> SEQ ID NO 10
<211> LENGTH: 19
<212> TYPE: PRT
<213> ORGANISM: Porcine circovirus

<400> SEQUENCE: 10

Pro Arg His His Tyr Arg Pro Arg Arg Lys Asn Gly Ile Phe Asn Thr
1               5                   10                  15

Thr Leu Ser


<210> SEQ ID NO 11
<211> LENGTH: 233
<212> TYPE: PRT
<213> ORGANISM: Artificial Sequence
<220> FEATURE:
<223> OTHER INFORMATION: This is an amino acid sequence for porcine
      circovirus type 2, open reading frame 2.

<400> SEQUENCE: 11

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30
```

-continued

```
Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Lys Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```